US007786257B2

(12) United States Patent
Murray et al.

(10) Patent No.: US 7,786,257 B2
(45) Date of Patent: Aug. 31, 2010

(54) SIGNAL-1/SIGNAL-2 BIFUNCTIONAL PEPTIDE INHIBITORS

(75) Inventors: Joseph S. Murray, Topeka, KS (US); Teruna J. Siahaan, Lawrence, KS (US); Yongbo Hu, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 1637 days.

(21) Appl. No.: 09/739,466

(22) Filed: Dec. 18, 2000

(65) Prior Publication Data
US 2005/0107585 A1    May 19, 2005

(51) Int. Cl.
*C07K 14/00* (2006.01)
(52) U.S. Cl. ........................... 530/325; 530/350
(58) Field of Classification Search .................. 530/325, 530/350
See application file for complete search history.

(56) References Cited
U.S. PATENT DOCUMENTS
5,540,926 A    7/1996    Aruffo et al.

FOREIGN PATENT DOCUMENTS
WO    WO 98/044129    10/1998

OTHER PUBLICATIONS

Corper, et al., "A Structural Framework for Deciphering the Link Between I-A$^{g7}$ and Autoimmune Diabetes," *Science*, vol. 288, pp. 505-511 (2000).
Schountz, et al., "MHC Genotype Controls the Capacity of Ligand Density to Switch T Helper (Th)-1/Th-2 Priming In Vivo," *The Journal of Immunology*, pp. 3893-3901 (1996).
Falcioni, et al., "Peptidomimetic Compounds That Inhibit Antigen Presentation by Autoimmune Disease-Associated Class II Major Histocompatibility Molecules," *Nature Biotechnology*, vol. 17, pp. 562-567 (1999).
Murray, Joseph S., "How the MHC Selects Th1/Th2 Immunity," *Immunology Today*, vol. 19, No. 4, pp. 157-163 (1998).
Murray, et al., "Major Histocompatability Complex (MHC) Class II Molecules Direct TCR-Specificity for Opposite Ends of the Same Immunogenic Peptide in TH1 or Th2 Responses," Department of Pharmaceutical Chemistry, and Department of Molecular Biosciences, The University of Kansas, pp. 1-20.
Murray, et al., "Major Histocompatability Complex Regulation of T Helper Functions Mapped to a Peptide C Terminus That Controls Ligand Density," *Eur. J. Immunol.*, vol. 24, pp. 2337-2344 (1994).
Murray, et al., "High-Density Presentation of an Immunodominant Minimal Peptide on B Cells is MHC-Linked to Th1-like Immunity," *Cellular Immunology*, vol. 166, pp. 9-15 (1995).
Salomon, et al., "B7/CD28 Costimulation is Essential for the Homeostasis of the CD4+CD25+ Immunoregulatory T Cells that Control Autoimmune Diabetes," *Immunity*, vol. 12, pp. 431-440 (2000).
Ruedl, et al., "The Antigen Dose Determines T Helper Subset Development by Regulation of CD40 Ligand," *Eur. J. Immunol.*, vol. 30, pp. 2056-2064 (2000).
Schountz, et al., "Unique T Cell Antagonist Properties of the Exact Self-Correlate of a Peptide Antigen Revealed by Self-Substitution of Non-Self-Positions in the Peptide Sequence," *Cellular Immunology*, vol. 168, pp. 193-200 (1996).
Edwards, et al., "Mapping the Intercellular Adhesion Molecule-1 and -2 Binding Site on the Inserted Domain of Leukocyte Function-associated Antigen-1," *The Journal of Biological Chemistry*, vol. 273, No. 44, pp. 28937-28944 (1998).
Dessen, et al., "X-Ray Crystal Structure of HLA-DR4 (DRA 0101, DRB1 0401) Complexed with a Peptide from Human Collagen II," *Immunity*, vol. 7, pp. 473-481 (1997).
Yoon, et al., "Control of Autoimmune Diabetes in NOD Mice by GAD Expression of Suppression in β Cells," *Science*, vol. 284, pp. 1183-1187 (1999).
Amrani, Abdelaziz, "Progression of Autoimmune Diabetes Driven by Avidity Maturation of a T-Cell Population," Letters to Nature, Nature Aug. 17, 2000, Vol. 406, p. 739-742, 2000 Macmillan Magazines, Ltd.
Anderson, Meagan E., "Targeting ICAM-1/LFA-1 Interaction for Controlling Autoimmune Diseases: Designing Peptide and Small Molecule Inhibitors," Peptides, 2003, Science Direct, p. 487-501, Elsevier.
Garkoui, Arash, "TCR-Independent Pathways Mediate the Effects of Antigen Dose and Altered Peptide Ligands on Th Cell Polarization," 1999, p. 1923-1930, The American Association of Immunologists.
Murray, Joseph S., "How the MHC Selects Th 1/Th2 Immunity," Viewpoint, Apr. 1998, Vo. 19 No. 4, p. 157-162.
Boyle et al., "Enhanced Responses to a DNA Vaccine Encoding a Fusion Antigen that is Directed to Sites of Immune Induction", Nature, Mar. 1998, vol. 392, pp. 408-411.
Huang et al., "Enhanced Antitumor Immunity by Fusion of CTLA-4 to a Self Tumor Antigen", Blood, Dec. 1, 2000, vol. 96, No. 12, pp. 3663-3670.

*Primary Examiner*—Christina Chan
*Assistant Examiner*—F. Pierre VanderVegt
(74) *Attorney, Agent, or Firm*—Stinson Morrison Hecker LLP

(57) ABSTRACT

A novel peptide sequence having the general formula AB wherein each of A and B represent a chain of amino acid residues and wherein said A chain is capable of binding with a major histocompatibility complex on an antigen presenting cell, and wherein said B chain is capable of binding with a Signal-2 receptor on an antigen presenting cell. Preferred forms of the peptide sequence further include an X chain positioned intermediate the A chain and the B chain. Moreover, preferred forms include an A chain which has at least about 10% sequence homology with a Signal-1 moiety, or is a peptidomimetic of a Signal-1 moiety, said B chain has at least 10% sequence homology with a Signal-2 receptor moiety, or is a peptidomimetic of a Signal-2 receptor moiety, and wherein the X chain has at least one amino acid residue, or is a peptidomimetic of that amino acid residue. Advantageously, the novel peptide sequence is capable of shifting a type-1 immune response to a type-2 immune response or from a type-2 immune response to a type-1 immune response.

51 Claims, 23 Drawing Sheets

*In vitro* conditions

EGAD-BPI Rx   PBS Rx

SIGNAL-1/SIGNAL-2 BIFUNCTIONAL PEPTIDE INHIBITORS

SEQUENCE LISTING

A printed Sequence Listing accompanies this application, and has also been submitted with identical contents in the form of a computer-readable ASCII file on a floppy diskette and a CDROM.

BACKGROUND OF THE INVENTION

1. Field of the Invention

The present invention concerns immune responses initiated by the recognition of a peptide:MHC complex on the surface of antigen presenting cells by T-cells. The present invention also concerns immune responses initiated by the binding of a Signal-2 moiety to its complement protein on the surface of an antigen presenting cell. More particularly, the present invention concerns the immune responses initiated by the recognition of the peptide:MHC by the T-cell and by the binding of a Signal-2 moiety to its complement protein. Still more particularly, the present invention concerns the modification of the typical immune response generated by a particular individual in response to this binding. Most particularly, the present invention concerns the conjugation of peptides derived from the peptide portion of the peptide:MHC complex to the preferred Signal-2 moiety in order to modify or shift a given immune response from type-1 to type-2 or from type-2 to type-1. This may include specific phenotypes of regulatory T-cells including suppressor T-cells.

2. Description of the Prior Art

Autoimmune diseases are characterized by the activation of T-cells against self-antigens. These T-cells then destroy cells presenting these antigens. For example, insulin-dependent diabetes mellitus (IDDM, also called Type-I diabetes) is characterized by the activation of T-cells against the insulin-producing cells of the pancreas and their subsequent destruction by these T-cells. The diseases and conditions associated with autoimmune responses are strongly associated with specific subtypes (alleles) of cell surface proteins called major histocompatability complex (MHC) class II molecules. MHC molecules bind fragments (peptides) of proteins from infectious agents, allergens, and selfproteins, and this MHC:peptide complex is the structure that T-cells recognize with their receptor (called the T-cell receptor, or TCR). The MHC:peptide complex is displayed on the surfaces of other cells of the immune system (i.e., B cells, dendritic cells and macrophages) which are called antigen presenting cells (APC). In order for an immune response to ensue, the major regulatory cell of the immune system, the undifferentiated T-cell, must be presented with small breakdown products (peptides) of the foreign invader. This presentation occurs on the surface of the APC. The T-cell must then interact with the APC, and this interaction stimulates the T-cell to divide and differentiate to produce molecules that attack, either directly or indirectly, cells displaying the same or highly similar MHC:peptide complex. It is well known that the genes that encode the MHC molecules are extremely variable within the species, and the different MHC alleles prefer to bind some peptides over others. Along with other genetic and environmental factors, the existence of different MHC alleles helps to explain why some members of a species develop conditions such as autoimmune diseases, allergies, asthma, and even certain infectious diseases, while others remain seemingly unaffected, or immune, to the same substances. Other differences arise because cell surface proteins distinct from the peptide:MHC complex must also bind to specific receptors on the T-cell. These other protein:protein pairs at the interface of the T-cell and APC membranes provide a costimulatory signal, known as Signal-2 which, along with the signal generated by the TCR recognition of the MHC:peptide complex (known as Signal-1), initiates an immune response.

A defining stage of the immune response is the differentiation of CD4$^+$ T-cells into either type-1 helper T-cells (T$_H$1 cells) or type-2 helper T-cells (T$_H$2 cells) as a result of the two signals. These two subtypes of T$_H$ cells and the regulatory network of cells that they selectively activate are well-known correlates of human health conditions and disease states. Differentiation into T$_H$1 cells results in predominantly cell-mediated immunity while differentiation into T$_H$2 cells results in predominantly humoral immunity. Each of these immunity types helps to protect the body against different types of invasion. Type-1 immunity protects the body against intracellular pathogens such as bacteria, but is also implicated in organ-specific autoimmune diseases. Type-2 immunity is important for protection against extracellular parasites, but is associated with allergic reactions as well. Development of T$_H$1 cells is driven by a cytokine called interleukin-12, which is produced by immune cells known as macrophages and dendritic cells. Interleukin-12 induces or stimulates the naive T-cell (CD4$^+$ T-cells) to produce interferon-γ (IFN-γ) and interleukin-2 (IL-2). These two cytokines (IL-2 and IFN-γ) are involved in classic cell-mediated functions such as clonal expansion of cytotoxic T-lymphocytes (CTLs), macrophage activation, and class switching to IgG isotypes that mediate complement lysis of sensitized cells. Commitment to a T$_H$1 immune response is enhanced by the presence of IFN-γ which up-regulates expression of the interleukin-12 (IL-12) receptor while inhibiting the development of T$_H$2 cells. T$_H$2 immunity results from the production of interleukin-4 (IL-4) by the naive T-cell. IL-4 induces T$_H$2 development and the subsequent production of interleukins-4 (IL-4), -5 (IL-5), -10 (IL-10), and -13 (IL-13). IL-4 also operates to down-regulate expression of the IL-12 receptor on developing cells, thereby inhibiting T$_H$1 development and helping undifferentiated T-cells to commit to T$_H$2 cell development. Additionally, IL-4 and IL-5 are known to activate B cells and switch to neutralizing antibody (IgG1 in the mouse) and IgE, the initiator of immediate hypersensitivity.

In order for either of these immune pathways to be activated, a two-signal mechanism is required to fully activate the T-cell. Signal-1 (S-1) occurs when the T-cell antigen receptor (TCR) recognizes the peptide:MHC-II complex on the surface of an antigen presenting cell (APC). This first signal passes through the T-cell receptor and initiates a cascade of tyrosine phosphorylation/dephosphorylation events mediated by kinases and phosphatases and leads to the activation of Ca$^{++}$ flux, nuclear factor of activated T cells (NF-AT) and NFκB transcription factors. These factors enter the nucleus of the T-cell and bind to promoters of genes responsible for effector functions. Signal-2 (S-2) arises from the binding of Signal-2 receptors to their ligands on the surface of an APC. Signal-2 receptors include CD28 and its ligand B7 as well as LFA-1 and its ligand ICAM-1. When a Signal-2 receptor and its ligand form a complex at the interface between the T-cell and APC receptor membranes, a series of signaling events occur. These events include serine/threonine phosphorylation/dephosphory-lation and activation of guanine nucleotide exchange factors that activate adapter proteins with GTPase activity. These signaling events activate a separate set of transcription factors. The signal delivered through the CD28: B7 complex is distinct from that delivered from the ICAM-1:LFA-1 complex, particularly with respect to the differentiation of CD4⁺ T-cells into $T_H1$ versus $T_H2$ effector populations. When the predominant binding occurs between LFA-1 and ICAM-1, the CD4⁺ T-cell differentiation favors $T_H1$ cells which are abundant producers of IL-2 and IFNγ, the preeminent initiators of inflammatory immune responses including delayed-type hypersensitivity (DTH), immunity to intracellular pathogens, and several autoimmune diseases. When the predominant binding occurs between CD28 and B7, the CD4⁺ T-cells differentiate into $T_H2$ cells. In contrast to $T_H1$ cells, $T_H2$ cells do not produce abundant IL-2 or IFNγ cytokines, but instead release the mediators of immediate-type hypersensitivity such as allergy and asthma, i.e., IL-4, IL-5, IL-10, and IL-13. Thus, the ability to manipulate the relative contribution of the complex providing the second signal has a profound effect on the type of immune response that is elicited against a given self-tissue antigen.

The associations between the TCR and APC occur at a specialized junction or interface between the TCR and the APC called the immunological synapse. An immune synapse is depicted schematically in FIG. 1. This immune synapse can be defined as the organized structure of activation molecules that assemble at the interface between the T-cell and the APC. Like a synapse in the nervous system, the immune synapse is a close association between cellular membranes. In order for an immune response to ensue, the major regulatory cell of the immune system, the undifferentiated T-cell must be presented with small breakdown products (peptides) of the foreign invader. In an unactivated T-cell, TCR and adhesion molecules are dispersed randomly on the T-cell membrane. The formation of the immunological synapse is an active and dynamic mechanism that allows T-cells to distinguish potential antigenic ligands. The immunological synapse consists of a central cluster of T-cell receptors surrounded by a ring of adhesion molecules. The stable formation of the immune synapse requires adhesion molecules such as LFA-1 and the peptide-recognition receptor (TCR) to form a doughnut-like structure with the TCR on the inside and LFA-1 on the outside. During activation, the TCR and LFA-1 molecules pass by each other within the T-cell lipid bilayer during the formation of the doughnut-like structure (this process is called translocation). If these molecules do not translocate within the immune synapse then the T-cell signal is not fully received and a different program of gene activity may ensue within the T-cell. This can drastically effect the immune response, especially if the T helper cell deviates from a gene program that would lead to IFNγ release ($T_H1$ cells and type-1 immunity) to a program that ultimately activates IL-4 production (i.e., $T_H2$ cells and type-2 immunity).

In more detail, to activate the pathway leading to $T_H1$ dominance, the TCR recognizes the peptide:MHC-II complex and sends Signal-1 to the T-cell. Additionally, LFA-1 binds to ICAM-1, and these molecules, along with the peptide:MHC-II complex, translocate to form the end-stage immune synapse. This leads to the effective expression of the CD40 ligand (CD154) by the uncommited $T_H$ cell. CD40 interaction (expressed on the antigen presenting cell) with its ligand generates NFκB up-regulation of the inflammatory cytokine, IL-12. IL-12 then binds to its receptor on the undifferentiated $T_H$ cell and initiates the $T_H1$ program, including the up-regulation of the transcription regulators, Stat4 and Tbet. This leads to $T_H1$ dominance against the autoantigen (e.g., glutamic acid decarboxylase, GAD65), which was initiated by the GAD65 peptide component of the TCR:peptide: MHC-II complex. For the pathway leading to $T_H2$ dominance, the TCR can recognize the same peptide:MHC-II complex, thereby sending Signal-1. However, in this case, a weaker strength of Signal-1 and/or altered or blocked binding between Signal-2 moieties leads to an altered form of the end-stage immune synapse. Likely, this lower strength of Signal-1 or distinct participation of the LFA-1 second signal leads to this different result, i.e., dominant $T_H2$ differentiation. For example, the altered immune synapse can dictate that the CD40 ligand is not expressed and IL-12 is therefore not released by the APC. This pathway is schematically represented in FIG. 2. Here, IL-4 appears to accumulate, thereby leading to the up-regulation of Stat6 and GATA-3 within the T-cell and hence commitment to a $T_H2$ pattern of differentiation.

A major goal of modern applied immunology is to be able to switch from $T_H1$-dominant immunity (e.g., as seen in autoimmune diseases and transplant rejection) to $T_H2$ responses against these same tissue antigens. In other cases, it would be extremely valuable to replace weak $T_H2$ immunity with $T_H1$ dominance leading to strong T-cell proliferation and the effective generation of cytotoxic T-cells (CTL). These cases may include chronic viral illnesses, like hepatitis-C and AIDS; and could include certain cancers like melanoma. Accordingly, what is needed in the art is modifiers of these immune responses so that type-2 immunity can be replaced with type-1 immunity or type-1 immunity can be replaced with type-2 immunity, as desired in order to combat different human disease states or health conditions.

SUMMARY OF THE INVENTION

The present invention solves the problems found in the prior art and provides a distinct advance in the state of the art. Briefly, the present invention embraces a peptide which includes a portion of a Signal-1 moiety at one end and a portion of a Signal-2 moiety at the other end. These two ends can be directly connected to each other or connected via a flexible, non-substrate linker. This conjugation of the peptide portions directly and via a linker into a continuous peptide chain produces a new class of immunotherapeutic peptides termed bifunctional peptide inhibitors (BPI). These BPI are based upon the two signal mechanism of T-cell activation and link Signal-1 and Signal-2 moieties in order to alter T-cell activation. In other words, the present invention provides a method of modulating T-cells and subsequent immunity in a very specified manner such that only specific disease-associated populations of these cells are targeted by the products of the present invention. Thus, the present invention leaves necessary components of the intact immune system to operate in their nominal protective manner.

In more detail, the present invention describes constructing a peptide sequence having a TCR epitope of interest (a Signal-1 moiety) at one end and a peptide derived from the protein:protein interaction (the Signal-2 moiety) which generates Signal-2. These two peptide sequences can be connected via a flexible linker which couples the Signal-1 moiety to the Signal-2 moiety or can be directly linked together. In some cases, the linkage between the two peptides sequences may include flanking residues from each portion. The combination of the Signal-1 moiety coupled with the Signal-2 moiety constitutes a BPI. Accordingly, once a TCR epitope of interest is identified and the desired immune response (type-1 or type-2) determined, a BPI according to the present invention, can be generated.

As noted above, an important stage of the immune response is the differentiation of CD4⁺ T-cells into either type-1 helper T-cells ($T_H1$ cells) or type-2 helper T-cells ($T_H2$ cells). Differentiation into $T_H1$ cells results in predominantly cell-mediated immunity while differentiation into $T_H2$ cells results in predominantly humoral immunity. Each of these immunity types help to protect the body against different types of invasion. $T_H1$ cells protect the body against intracellular pathogens such as bacteria, and are also implicated in organ-specific autoimmune diseases. $T_H2$ cells are important for protection against extracellular parasites as well as allergic reactions. Development of $T_H1$ cells is driven by a cytokine called interleukin-12, which is produced by immune cells known as macrophages and dendritic cells. Interleukin-12 induces or stimulates the naive T-cell to produce interferon-γ (IFN-γ) and interleukin-2 (IL-2). These two cytokines (IL-2 and IFN-γ) are involved in classic cell-mediated functions such as clonal expansion of cytotoxic T-lymphocytes (CTLs), macrophage activation, and class switching to IgG isotypes that mediate complement lysis of sensitized cells. Commitment to a $T_H1$ immune response is enhanced by the presence of IFN-γ which up-regulates expression of the interleukin-12 (IL-12) receptor while inhibiting the development of $T_H2$ cells. This pathway is shown schematically in FIG. 3.

$T_H2$ immunity results from the production of interleukin-4 (IL-4) by the naive T-cell. IL-4 induces $T_H2$ development and the subsequent production of interleukins 4 (IL-4), 5 (IL-5) and 13 (IL-13), through activation of the transcription regulator Stat6. IL-4 also operates to down-regulate expression of the IL-12 receptor on developing cells, thereby inhibiting $T_H1$ development and helping undifferentiated T-cells to commit to $T_H2$ cell development. Additionally, IL-4 and IL-5 are known to activate B cells and switch to neutralizing antibody (IgG1 in the mouse) and IgE, the initiator of immediate hypersensitivity. Again, a schematic representation of this process is depicted in FIG. 2.

As noted above, a two-signal mechanism is required to fully activate the $T_H$ cell. Signal-1 occurs when the T-cell antigen receptor (TCR) recognizes or engages the peptide:MHC-II complex on the surface of an antigen presenting cell (APC). This first signal is transmitted through the T-cell receptor and initiates a cascade of tyrosine phosphorylation/dephosphorylation events mediated by kinases and phosphatases and leads to the activation of $Ca^{++}$ flux, NF-AT and NFκB transcription factors. These factors enter the nucleus of the T-cell and bind to promoters of genes responsible for effector functions. Signal-2 arises from the binding of a Signal-2 receptor on the T-cell to its protein ligand on the APC. Signal-2 receptors include CD28 and its ligand B7 as well as LFA-1 and its ligand ICAM-1. When a Signal-2 receptor and its ligand form a complex at the interface between the T-cell and APC membranes, a series of signaling events occurs including serine/threonine phosphorylation/dephosphorylation along with actuation of guanine nucleotide exchange factors that activate adapter proteins with GTPase activity. These signaling events activate a separate set of transcription factors. The signal delivered through the CD28:B7 complex is distinct from that delivered from the ICAM-1:LFA-1 complex, particularly with respect to the differentiation of $CD4^+$ T-cells into $T_H1$ versus $T_H2$ effector populations. A schematic representation of this signaling is provided herein as FIG. 4. When the predominant binding occurs between LFA-1 and ICAM-1, the $CD4^+$ T-cells differentiate into $T_H1$ cells. The $CD4^+$ T-cells of the $T_H1$ differentiation state are abundant producers of IL-2 and IFNγ, two cytokines that are the preeminent initiators of inflammatory immune responses, such as delayed-type hypersensitivity (DTH), immunity to intracellular pathogens, and several autoimmune diseases. When the predominant binding occurs between CD28 and B7 (i.e., decreased LFA-1:ICAM-1 signaling), the $CD4^+$ T-cells differentiate into $T_H2$ cells. In contrast to $T_H1$ cells, $T_H2$ cells do not produce IL-2 and IFNγ cytokines, but instead release the mediators of immediate-type hypersensitivity such as allergy and asthma, i.e., IL-4, L-5, IL-10, and IL-13. Thus, the ability to manipulate the relative contribution of the complex providing Signal-2 has a profound effect on the type of immune response that is elicited against a given self-tissue antigen.

The associations between the TCR and APC occur at a specialized junction called the immunological synapse (shown in FIG. 1). In order for the immune response to proceed, the undifferentiated $T_H$ cell, must be presented with peptides of the foreign invader on the surface of the APC. In an unactivated T-cell, TCR and adhesion molecules are dispersed randomly on the T-cell membrane. The formation of the immunological synapse is an active and dynamic mechanism that allows T-cells to distinguish potential antigenic ligands. The immunological synapse consists of a central cluster of T-cell receptors surrounded by a ring of adhesion molecules. This arrangement is depicted schematically in FIG. 1. In this figure, the TCR:peptide:MHC-II complex is in the center of the dark circle which represents the protein:protein pair constituting the Signal-2 receptor and the Signal-2 ligand. The stable formation of the immune synapse requires adhesion molecules such as LFA-1 and the peptide-recognition receptor (TCR) to form a doughnut-like structure with the TCR on the inside and LFA-1 on the outside. During activation, the TCR and LFA-1 molecules actually translocate past one another within the T-cell lipid bilayer. If these molecules do not translocate within the immune synapse then the T-cell signal is not fully received and a different program of gene activity may occur within the T-cell. This can drastically effect the immune response, especially if this causes the T helper cell ($T_H$) to deviate from a gene program leading to a $T_H1$ immune response to a program that activates a $T_H2$ immune response. As shown in FIG. 2, an interpretation of the BPI mechanism suggests that BPI bind to both the MHC-II and second signal ligands. This effectively tethers the MHC-II:peptide and ICAM-1 molecules thereby preventing the translocation step of immune synapse formation.

In one aspect of the present invention, known TCR epitopes are used as the first peptide portion of the BPI. In this manner, minimal peptide sequences that are potent immunogens are utilized. These minimal peptide sequences (e.g. antigenic peptides) effectively engage the TCR involved in immune responses of interest (i.e. autoimmune diseases, infectious diseases, allergies, cancers, etc). There are already many known TCR epitopes of interest (Signal-1 moieties) and their sequences have been defined in the literature. A partial list of some representative Signal-1 moieties is provided in Table 1. This list is by no means exhaustive as there are potentially thousands of Signal-1 moieties.

In another aspect of the present invention, TCR epitopes of interest are identified so that the first portion of the BPI can be synthesized. In this aspect, these dominant TCR epitopes have been so determined by previous art and the sequences are available in the literature. The peptide to which a given T-cell response is focused upon, (e.g., the response against the diabetes-associated antigen GAD65) is identified by the fact that most effector T-cells respond to this portion of the antigen and not other portions. In mouse model systems, animals are immunized with the whole protein antigen. Next, T-cells are removed after the antigen has primed the immune system. These T-cells are placed separately in cultures with short overlapping peptides of the antigen. Most of the response will be to a single peptide and this is the dominant TCR epitope. In humans, T-cells are first cloned from patients. These cloned T-cells are placed separately in cultures with overlapping peptides (again, representing individual portions of the antigen involved, e.g., HIV-1, p24 (SEQ ID No. 8)). Again, the peptide to which most T-cell clones respond is the dominant TCR epitope. The foregoing is described by Schountz et al., *MHC Genotype Controls the Capacity of Ligand Density to Switch T Helper (Th)-1/Th-2 Priming In Vivo*, 157 The Journal of Immunology 3893-3901 (1996), the teachings and content of which are hereby incorporated by reference herein.

In another aspect of the present invention, peptides derived from Signal-2 receptors are used to alter interactions between the nominal receptors on T-cells and their complementary ligands on the APC surface. Table 3 includes a representative list of some known Signal-2 receptor moieties. Of course, those of ordinary skill in the art will be able to identify other Signal-2 moieties not listed therein, as this list is representative and not all-inclusive.

Another aspect of the present invention is the linking of the TCR epitope (i.e. the Signal-1 moiety) to a Signal-2 receptor peptide mimic (i.e., the Signal-2 moiety) in order to modify the resultant immune response. This linkage can be between the Signal-1 moiety and the Signal-2 moiety directly, or through flanking residues. Alternatively, this linking can be done via a linker which is positioned between the Signal-1 moiety and the Signal-2 moiety. The linker could be any amino acid including naturally occurring or chemically synthesized amino acids. Preferably, non-substrate amino acids will be used due to their resistance to protease attack. Still more preferably, the linker will comprise a non-substrate amino acid alternating with a small or hydrophilic amino acid. Even more preferably, the linker is synthesizable as one continuous sequence along with the Signal-1 and Signal-2 moieties, which flank the linker at each respective end. Still more preferably, the linker has the general formula $(A,B)_X$, wherein A and B are amino acid residues, and the A amino acid residue is individually and respectively selected from the group consisting of aminocaproic acid, aminohexanoic acid, aminododecanoic acid, and β-alanine, and the B amino acid residue is a small or hydrophilic amino acid. In this formula, X can range from 1 to 100. A particularly representative B residue is glycine. In this embodiment, a linker could potentially have aminocaproic acid (Ac), aminohexanoic acid (Ahx), aminododecanoic acid (Ado), and β-alanine (βA) alternating with glycine residues (G) (e.g., Ac-G-Ahx-G-Ado-G-βA). The choice of the residues used to construct the linker can be based upon the desired length of the linker as well as steric hindrance considerations. One preferred linker comprises alternating Ac and G residues. This linker can be lengthened or shortened by the inclusion of the other amino acid residue choices (Ahx, Ado, βA). Some representative linkers are included in Table 2 as SEQ ID Nos. 26-29.

Approximately $10^9$ different TCR account for protective immunity to the universe of infectious agents and contain the repertoire of TCR that may turn against self in autoimmune diseases. Moreover, the TCR are also specific for potential tumor antigens and the myriad of allergenic substances in the environment. By changing the TCR epitope of a given BPI we direct the immunomodulating capacity of the BPI to a select group of TCR. In other words, the selection of a TCR epitope to incorporate into the BPI targets T-cells that are involved in a particular human disease in a highly specific fashion. For example, incorporating the GAD65 epitope into a BPI targets autoaggressive T-cells involved in the induction of type-1 diabetes. This targeting to specific TCR allows that T-cells necessary for immunity to infectious agents or cancers will not be significantly compromised. Thus, BPI offer the possibility to specifically modulate T-cell immunity to one antigen while leaving intact the T-cell repertoire necessary for protective immunity to infectious agents and developing cancers.

As noted above, the Signal-1 moieties of the present invention are preferably derived from TCR epitopes and a list of representative known epitopes is provided in Table 1 wherein these known epitopes are presented as SEQ ID Nos. 1-25. When a derivative of a TCR epitope is used to construct the BPI, preferably, the TCR epitope selected will be correlated with a known health condition or disease state. When using one of the representative peptides shown in Table 1 to construct the BPI, it is preferred that the peptides include a sequence having at least about 10% sequence homology with a sequence selected from the group consisting of SEQ ID Nos. 1-25. More preferably, the peptide will have at least 30% sequence homology with a sequence selected from the group consisting of SEQ ID Nos. 1-25. More preferably, the peptide will have at least 50% sequence homology with a sequence selected from the group consisting of SEQ ID Nos. 1-25. Even more preferably, the peptide will have at least 70% sequence homology with a sequence selected from the group consisting of SEQ ID Nos. 1-25. Most preferably, the peptide will have at least about 95% sequence homology with a sequence selected from the group consisting of SEQ ID Nos. 1-25. Of course, it is also well known in the art to use peptidomimetics to construct moieties having similar functions as the peptides derived from the TCR epitopes. In this respect, the teachings of Falcioni et al. in *Peptidomimetic Compounds That Inhibit Antigen Presentation by Autoimmune Disease-Associated Class II Major Histocompatability Molecules*, 17 Nature Biotechnology, 562-567 (1999), are incorporated by reference herein. Accordingly, all or part of this Signal-1 moiety portion of the BPI can include such peptidomimetics. Preferably, the peptidomimetic will be a mimetic of a peptide selected from the group consisting of SEQ ID Nos. 1-25. Alternatively, the Signal-1 moiety will be a derivative of a TCR epitope or a peptide selected from the group consisting of SEQ ID Nos. 1-25. At any rate, it is desired that this first portion of the BPI (or the portion responsible for initiating the first signal) be capable of binding with a major histocompatability complex (MHC) on an antigen presenting cell (APC). Furthermore, it is preferred that this resulting peptide:MHC complex be capable of engaging important TCR and initiating some form of the signal to the T-cell.

As noted above, the peptides used on the side of the linker opposite the Signal-1 moiety are preferably derived from Signal-2 receptors. This second portion of the BPI is connected to the first portion either directly or via the linker. In preferred forms, the second portion includes a sequence having at least about 10% sequence homology with a sequence selected from a group consisting of SEQ ID Nos. 30-41. More preferably, the second portion peptide has at least about 30% sequence homology with a sequence selected from the group consisting of SEQ ID Nos. 30-41. Still more preferably, the second portion peptide has at least about 50% sequence homology with a sequence selected from the group consisting of SEQ ID Nos. 30-41. Even more preferably, the second portion peptide has at least about 70% sequence homology with a sequence selected from the group consisting of SEQ ID Nos. 30-41. Most preferably, the second portion peptide includes a sequence having at least about 95% sequence homology with a sequence selected from the group of SEQ ID Nos. 30-41. As with the first portion, peptidomimetics can be used in place of all or some of the amino acid residues of the second portion. In preferred forms the peptidomimetic of the second portion will be a mimic of a peptide selected from the group consisting of SEQ ID Nos. 30-41. Alternatively, the second portion of the BPI will comprise a derivative of a peptide selected from the group consisting of SEQ ID Nos. 30-41. Similar to the first portion, it is preferred that the second portion be capable of binding with a complementary ligand (e.g. the Signal-2 ligand) on an antigen presenting cell.

For example, when a peptide derived from LFA-1 is used as this Signal-2 moiety of the BPI, it should bind to ICAM-1 on the surface of the APC. Additionally, it is preferred that this binding with the Signal-2 ligand on the APC inhibits or alters the binding of the moiety's parent receptor (on the T-cell) to this same APC ligand.

As explained above, the immune response involves a two signal mechanism and the purpose of the present invention is to modify a given immune response, e.g., from type-1 immunity to type-2 immunity or from type-2 immunity to type-1 immunity. This modification or shifting of immune response phenotype is brought about by BPI according to the present invention. It is preferred in some cases for the BPI to modify an immune response from a $T_H1$ dominated or cytolytic immune response to a $T_H2$ dominated response; and, in other cases, it is preferred for the BPI to modify an immune response from a $T_H2$ dominated response to a $T_H1$ or cytolytic dominated response. In some cases, BPI may operate via the activation of very specific T-cell phenotypes, e.g., peptide-specific suppressor T-cells. In contrast to the nominal situation where an antigen stimulates the system toward a $T_H1$ response (depicted in FIG. 2), the response generated when a BPI similar to the GAD 65-CD11a BPI is introduced into the immune synapse is quite different and operates to shift the response from type-1 to type-2. This situation is depicted schematically in FIG. 2. In this manner, a BPI comprising a Signal-1 moiety, a flexible, non-substrate linker, and a Signal-2 moiety is formed and introduced into the immune synapse. The TCR recognizes the peptide:MHC complex on the APC and initiates the first signal. However, the second portion of the BPI (the Signal-2 moiety) blocks the typical Signal-2 interaction occurring between LFA-1/ICAM-1, (or for other BPI:CTLA-4/B7, or CD40L/CD40, or FasL:Fas) and the translocation of the TCR into the central cluster. Depending on whether the LFA-1/ICAM-1 or CTLA-4/B7 interaction is targeted by the specific BPI construction, perhaps by tethering the MHC-II:peptide complex to the second signal ligand, the signal will be altered in a different direction of differentiation. For example, when the Signal-2 peptide portion of the BPI is derived from LFA-1, this would favor a decrease in CD40-ligand expression and hence, a lack of IL-12 release. By contrast, IL-4 released during the initial T-cell activation will accumulate to higher levels surrounding the synapse. This accumulation of IL-4 leads to Stat6 and GATA-3 up-regulation in the naive T-cell and ultimately to commitment to a type-2 pattern. Alternatively, when the Signal-2 moiety peptide portion of the BPI is derived from CTLA-4, the normal binding of CTLA-4 and CD-28 to B7 ligands is affected and thus more CD40 ligand is expressed (i.e., a greater role for high affinity LFA-1:ICAM-1 is dictated by blocking the B7 receptors); hence, the release of IL-12 increases. Interleukin-12 induces or stimulates the naive T-cell to produce more IFN-γ and IL-2, thus providing a positive feedback toward type-1 immunity. These two cytokines (IL-2 and IFN-γ) are involved in classic cell-mediated functions such as clonal expansion of cytotoxic T-lymphocytes (CTLs), macrophage activation, and class switching to IgG isotypes that mediate complement lysis of sensitized cells. Such responses are hallmarks of protective immunity against human viral diseases. It will also operated to link TCR epitopes to the receptor for Fas. Since Fas:FasL interaction governs apoptosis, it will be possible to increase the frequency of specific TCR-bearing cells by blocking the apoptotic event. This will be important for BPI design against HIV, HPV, HCV, and cancers.

Thus, an important aspect of the present invention is that tethering a specific TCR epitope to a Signal-2 receptor peptide mimic leads to alteration of T-cell differentiation involving T-cells bearing only these receptors and/or T-cell populations indirectly linked to these peptide specific subsets. The ability to block or alter T-cell responses to a given immunodominant peptide antigen would offer extremely precise treatments for immunopathological conditions. A major drawback to current immunotherapies is that broad specificities of T-cells are affected leaving the host more susceptible to infections and cancers. The BPI of the present invention should block and/or alter only the desired T-cell population and subsequent responses that depend on these initial T-cells. Also, BPI will target a specific TCR-bearing population for activation toward a desired effector function.

In another aspect of this invention, the relative strength of signal generated by the T-cell-APC interaction has an affect on whether the ultimate immune response is a type-1 or a type-2 response. In this regard, the teachings of Murray in *How the MHC Selects $T_H1/T_H2$ Immunity,* 19 Immunology Today 157-163 (1998) are hereby incorporated by reference.

In another aspect of the present invention, an immune response is modified by contacting an APC with a peptide capable of binding to an MHC and to a Signal-2 ligand on the APC and causing an altered signal to be transmitted to the T-cell. Thus, the immune response is deviated from the immune response generally associated with the immunogenic peptide and its corresponding antigen (i.e., infectious agent, self protein, or allergen).

In another aspect of the present invention, a peptide having the general formula AXB is provided. The A, X, and B represent a chain of amino acid residues wherein the A chain has at least about five residues and at least about 10% sequence homology with a TCR epitope, the B chain has at least four residues and at least about 10% sequence homology with a peptide derived from a Signal-2 moiety, and the X chain is a linker. The linker could be any amino acid including naturally occurring or chemically synthesized amino acids. Additionally, the X chain has at least one residue. It is possible to link A to B directly without X as well, although a linker of some size is preferred in order to span the distance between the MHC-II and second signal ligands on the APC surface. As noted above, preferably, non-substrate amino acids will be used due to their resistance to protease attack. Still more preferably, the linker will comprise a non-substrate amino acid alternating with a small or hydrophilic amino acid. Even more preferably, the linker is synthesizable as one continuous sequence along with the Signal-1 and Signal-2 moieties, which flank the linker at each respective end. Still more preferably, the linker has the general formula $(A,B)_x$, wherein A and B are amino acid residues, and the A amino acid residue is individually and respectively selected from the group consisting of aminocaproic acid, aminohexanoic acid, aminododecanoic acid, and β-alanine, and the B amino acid residue is a small or hydrophilic amino acid. In this formula, X can range from 1 to 100. A particularly representative B residue is glycine. In this embodiment, a linker could potentially have aminocaproic acid (Ac), aminohexanoic acid (Ahx), aminododecanoic acid (Ado), and β-alanine (βA) alternating with glycine residues (G) (e.g., Ac-G-Ahx-G-Ado-G-βA). The choice of the residues used to construct the linker can be based upon the desired length of the linker as well as steric hindrance considerations, hydrophobicity, charge, etc. One preferred linker comprises alternating Ac and G residues. This linker can be lengthened or shortened by the inclusion of the other amino acid residue choices (Ahx, Ado, βA). Some representative linkers are included in Table 2 as SEQ ID Nos. 26-29. Additionally, the X chain is positioned between the A chain and the B chain and the entire peptide can be synthesized as one continuous sequence. Some preferred sequences will have an A chain having at least about 10% sequence homology with any one of SEQ ID Nos. 1-25, an X chain having at least about 2% sequence homology with any one of SEQ ID Nos. 26-29, and a B chain having at least about 10% sequence homology with any one of SEQ ID Nos. 30-41. Preferably, the peptide is capable of shifting a type-1 response to a type-2 response, or vice versa. Of course, peptidomimetics may be synthesized to mimic any part of the BPI, including the linker. Preferably, the A chain binds to the MHC on an APC to form a peptide:MHC complex. This complex is capable of engaging the TCR on critical T-cell populations. Still more preferably, the B chain is capable of binding to a Signal-2 ligand on the APC at the same time as the formation of the peptide:MHC complex. This combined binding to the APC should be capable of altering the signal delivered to the T-cell. The combination of the first signal and the second signal are capable of fully activating a T-cell and by selecting the peptide used for the A chain and the peptide used for the B chain, the immune response can be deviated from its normal progression. In the case of a normally activated type-1 response leading to the up-regulation of $T_H1$ cells, the response can be altered to give a type-2 response leading to the up-regulation of $T_H2$ cells. In the case of a normally activated type-2 response leading to the up-regulation of $T_H2$ cells, the response can be altered to give a type-1 response leading to the up-regulation of $T_H1$ cells. Again, the A chain can be chosen based on the health condition normally associated with the sequence (for example, see Table 4).

In another aspect of the present invention, a method is provided for preparing a peptide for modulating immune responses. This method comprises the steps of selecting a first peptide sequence which has at least about 10% sequence homology with a sequence derived from a TCR epitope, selecting a second peptide sequence which has at least about 10% sequence homology with a sequence derived from a Signal-2 receptor moiety, selecting a third peptide sequence which is a flexible, non-substrate linker, and synthesizing the peptides as a continuous peptide chain. Preferably, the linker is flanked on one end with the peptide derived from the TCR epitope and flanked on the other end with the peptide derived from the Signal-2 moiety. Preferably, the first peptide sequence should be associated with a known health condition and be capable of binding with an MHC on an APC. Similarly, it is preferred that the second peptide sequence be capable of binding with a Signal-2 ligand moiety on the APC. The method can further comprise the step of contacting the nominal peptide immunogen with the TCR, thereby binding the first peptide sequence to the MHC and the second peptide sequence to the Signal-2 ligand, thereby generating APC bearing potent first and altered/blocked second signal ligands which activate a desired immune response.

Inherent in the BPI design is the antigen-specific moiety that a given T-cell population is activated to respond against (i.e., the TCR epitope), ultimately leading to the cascade of immune reactions that generate protective or in some cases pathologic immune responses. These epitopes when bound to major histocompatibility complex (MHC) molecules on the antigen presenting cell (APC) surface provide the Signal-1 of the two-signal mechanism of T-cell activation. Thus, an important consideration is the affinity of a given peptide for MHC molecules. This affinity was directly tested by the binding of biotinylated peptide to the cells that present the peptide: MHC complex to the T-cells in mouse and man. T-cell clones to possible peptide epitopes were generated and tested for binding to the immunodominant TCR of a response and specifically stimulate T-cell functions in vitro by the ELISPOT assay. Because modifications in the peptide residues that actually contact the TCR are part of the BPI development, it is also preferable that known crystallographic structures of the epitope bound to MHC molecules are available. This allows for precise three-dimensional predictions of how a particular amino acid substitution or mimetic will affect the actual structure encountered by the developing T-cells. However, in the absence of known crystal structures, it is possible to predict the shape of a hypothetical peptide:MHC structure based upon the available coordinates of other peptide:MHC structures. This predictability is partially due to established peptide binding motifs, that allow for prediction of which residues of the epitope fit most readily into the particular binding pockets of a given MHC allele. These predictions have been accomplished using two different alleles (I-$A^s$ and I-$A^b$) binding a collagen peptide wherein each polymorphic position of the I-A molecules were substituted with the known amino acids at these positions. The overall structure was based upon the published coordinates of a reference allele I-$A^k$ binding a different peptide. Thus, in cases where the 3D structure of a particular disease-associated epitope is not known, a structure for predicting where the TCR contacts the peptide by a similar allelic-substitution and modeling approach can still be generated. It is important to identify (or at least predict) these TCR contact positions. It is well-known that certain alterations to TCR-contact positions can change the functional differentiation of T-cells into the $T_H1$ or $T_H2$ types that can determine the course of immunity (see Murray, et al., Major Histocompatibility Complex (MHC) Class II Molecules Direct TCR-Specificity for Opposite Ends of the Same Immunogenic Peptide in $T_H1$ or $T_H2$ responses (unpublished manuscript, 2000); and Murray; 19 *Immunology Today* 157-163 (1998), the teachings of which are hereby incorporated by reference.

Specifically, it was verified that the peptide binds to MHC molecules on live APC. Briefly, spleen cell density-gradient fractions (from mice), or PBL, or APC lines (from humans) were incubated in round bottom 96-well plates with increasing concentrations of individual biotinylated peptides at 37° C., 5% $CO_2$ for 16 hours. Following binding of the BPI to the APC, Avidin-FITC was incubated with the cells on ice for 30 minutes, followed by biotinylated anti-Avidin for 1 hour, then again with Avidin-FITC. For BPI titrations, increasing concentrations (0.1-100 μM) of the biotinylated derivatives in sterile 0.5% BSA-PBS were incubated with the APC for 16 hours as above. As shown in FIG. 5, the GAD 65 BPI binds preferentially to NOD APC as predicted. The LFA-1 moiety or the GAD 65 moiety did not display this increased binding to the diabetes strain's APC. Three-color analyses used Cy-Chrome or PE-conjugated antibodies to known surface markers of APC that were commercially available. Avidin-FITC and biotinylated anti-Avidin detection of the bound peptide was as previously described in Murray et al., 24 *Eur. J. Immunol.* 2337-2344 (1994); Murray; 19 *Immunology Today* 157-163; and Schountz et al., 157 *The Journal of Immunology* 3893-3901 (1996). Slight modifications of this method were used to test peptide inhibition (i.e., peptide affinity) and cocapping to the MHC and ICAM molecules directly on the live APC surface. First, monoclonal antibodies (mAb) against MHC or ICAM molecules blocked BPI binding, therefore showing that the BPI binds to these molecules (FIG. 6). Unlabeled peptide was used in a competition assay to derive the relative affinity of the BPI for the APC and the ability of the BPI to crosslink the MHC and ICAM molecules on the APC was examined by cocapping ICAM with an anti-MHC mAb. Here, cells were incubated with the BPI. Next, an anti-MHC mAb was added. After 30 minutes at 37° C., the cells were transferred to ice and stained with PE-labeled anti-ICAM (FIG. 7).

Next, T-cell clones were generated for determination of TCR epitopes for later use in BPI. These experiments utilized CD4+ or CD8+ T-cell clones from humans or mice immunized against predicted TCR epitopes using previously described methods (Murray et al., 24 *Eur. J. Immunol.* 2337-2344 (1994); Murray; 19 *Immunology Today* 157-163; and Schountz et al., 157 *The Journal of Immunology* 3893-3901 (1996)). These clones were maintained by biweekly restimulation with irradiated histocompatible lymphocytes, the peptide, and recombinant IL2. To determine if a given TCR-epitope is effective for the activation to cytokine synthesis, an ELISPOT assay was used. Of course, other cytokine assays could also be used. For analysis, BPI that have been substituted at predicted TCR-contact positions will be used to determine which of these BPI variants are most effective in the inhibition of proliferation and cytokine release from individual clones as analyzed above. Predicted positions will be scanned with different amino acids or mimetics to alter the interaction with the TCR in the structures generated by molecular modeling.

Next, Molecular Dynamics/Energy Minimizations (MDEM) will be used to study the peptide conformations. MD simulations will be used in conjunction with crystallographic data to predict the solution conformations of the BPI. MDEM simulations can predict flexibility and conformational changes during binding of BPI to MHC-II and ICAM-1. Amino acid substitutions can also be introduced into the Signal-1 and/or Signal-2 moieties in order to favor simultaneous binding to both receptors, as first predicted by these model studies. The I-$A^{g7}$:BPI:D1 structure (see FIG. 8) is an example of using the crystal structure coordinates of a disease-associated peptide:MHC structure (I-$A^{g7}$:GAD65 peptide). For this figure, docking studies were performed on a Silicon Graphic Octane workstation using InSight II (MSI/Biosym). The LFA-1-ICAM-1 structure was taken from known diffraction coordinates and the I-$A^{g7}$:GAD65 peptide was from known coordinates. Of course, analogous methods can be used to model the BPI listed in Tables 1, 2, 3 and 4 for binding to the various MHC molecules of mouse and man.

The second stage in the BPI process is selection of peptide mimics of established second signal receptor molecules involved in the functional differentiation of T-cells. To determine these structures, the crystallographic structures and available models of the second signal receptors bound to their physiological ligands will be used to predict the regions of the receptors that make contact with the ligand. This approach was used to design the EGAD-BPI which can be depicted as

```
        (EIAPVFVLLE)-(AcGAcGAc)-(ITDGEATDSG)

GAD65(208-217)      linker      LFA-1(237-247)
```

These interactions can also be determined empirically by making site-directed changes in the second signal molecules and determining whether such mutant molecules still bind to the ligand in question. However, many of these studies have been performed with known second signal receptors, including LFA-1, CD28/CTLA4, CD40L, and CD95L. Molecular modeling studies will be used as above to model the interactions of these second signal moieties with their ligands separately and when the moiety is part of the BPI structure.

Once candidate BPI moieties that bind effectively to the MHC and second signal ligands and that alter T-cell functions in vitro were identified, these moieties were synthesized at opposite ends of relatively short synthetic peptides, connecting them by a non-proteolytic substrate linker of variable length. As described by the prototypical EGAD-BPI, the Signal-1 moiety (i.e., the disease-associated TCR epitope) was linked by this flexible linker to the Signal-2 receptor mimic peptide (i.e., a second signal receptor thought to be involved in $T_H1/T_H2$ differentiation. These synthetic peptides were generated by conventional methods of peptide synthesis. In some cases, BPI are tested for binding to isolated MHC and second signal ligands, and NMR, molecular modeling and crystallography are used to determine their exact 3D structures. Finally, it was determined whether a given BPI was biologically active in vivo. Mice were treated with the BPI and immune cells isolated and tested for cytokine production by ELISPOT (see FIGS. 9 & 10). Of course other cytokine assays will be well known to those of ordinary skill in the art and can be used in place of ELISPOT. In vivo models similar to the NOD.Scid model (i.e., human Scid, transgenic knockout strains, etc.) were used, with modifications necessary for each disease being examined, as a more stringent test of BPI efficacy. For example, in the case of the HIV-1 p24 TCR-epitope, human-Scid mice are used for the adoptive transfer experiments. In this experiment, T-cells from patients will first be cloned by conventional methods and stimulated with the BPI in vitro. Next, these cells will be transferred into the human-Scid mice and analyzed as with the EGAD-BPI in the NOD.Scid adoptive transfer experiment. Results from these experiments are given in FIGS. 11-13.

To synthesize the BPI, Fmoc chemistry on chlorotrityl resins was used. Protected amino acids were double coupled at 8-fold excess for 1 hour. Resins were DMF and MeOH washed and cleaved in Reagent R: TFA, EDTA, Thioanisole, Anisole. The TFA mixture containing the peptide in solution was precipitated in ether and washed extensively. Preparative HPLC of peptides was accomplished by a gradient of 0-80% acetonitrile in 0.1% TFA. Lyophilization of the various fractions and verification by MALDI-TOF using a Voyager mass spec (PerSeptive, Foster City, Calif.) yielded the synthetic peptide as a TFA salt. Modeling, crystallography and binding studies, as described above, were used to generate the predicted BPI complex structure.

In another example which tested the diabetes BPI in vivo, 15 million disease-linked lymphocytes (i.e., patient T-cells, or T-cell populations linked to the disease process) were injected with or without T-cells that received the BPI compound (in vivo or in vitro) and were expanded for 24 hours in recombinant IL-2. Some experiments will deplete specific subsets of the T-cells using mAb to CD154, CD25, CD62L, CD152, etc. and magnetic particles prior to adoptive transfer. T-cells (from mice or humans) treated with the individual moieties of the BPI will be used as negative controls along with $CD4^+$ cells from mice treated with saline alone (FIG. 9). For blocking spontaneous diabetes, five groups of ten female NOD mice (12 weeks of age) were used and monitored for nondiabetic blood glucose levels with a standard glucometer (AccuChek-complete, Roche Diagnostic). Each mouse was labeled and individually monitored for blood glucose levels weekly for the course of the experiment. The five groups received either (a) intravenous (i.v.) injection of the BPI (100 μg in 100 μl endotoxin-free saline/injection) at 8 weeks of age, (b) same dose GAD65 (208-217) epitope alone, (c) same dose CD11a (237-247) peptide alone, or (d) saline alone. For other systems, similar treatment groups involving the different Signal-1 and Signal-2 peptides and BPI will be used. Mice will be tested by challenging with the appropriate infectious agent or antigen depending upon the particular BPI in question.

To evaluate the disease process by immunohistology (see, e.g., FIG. 12A-D), spleen, pancreas, or other target organs, e.g., the CNS for the MDP peptide BPI, or lung for the RSV peptide BPI, were removed from euthanized mice of each group and prepared for histology by fixing in neutral buffered formalin and embedding in paraffin, or snap frozen in O.C.T. medium. For scoring inflammation, minimums of five sections from each mouse were used to assess the blocking affect of a given BPI. For characterization of standard T-cell markers on cellular infiltrates, biotinylated mAb to various cell surface antigens will be incubated individually with the Cryostat sections (2 hours), followed by avidin-alkaline phosphatase (Vector laboratories). Alternatively, cell subsets will be phenotyped by standard flow cytometry methods as described in Murray et al., 24 *Eur. J. Immunol.* 2337-2344 (1994); Murray; 19 *Immunology Today* 157-163; and Schountz et al., 157 *The Journal of Immunology* 3893-3901 (1996). Finally, the students t-test or ANOVA will be used to estimate the statistical significance of differences observed between groups and individual mice.

A few representative assembled BPI consisting of a Signal-1 moiety and a Signal-2 receptor moiety joined together via a linker are provided in Table 4 as SEQ ID Nos. 42-46. These representative BPI are operable for shifting specific immune responses from a type-1 to a type-2 response and vice-versa. Advantageously, other immune responses to other antigenic peptides will be preferably unaffected.

DETAILED DESCRIPTION OF THE PREFERRED EMBODIMENT

Figure 1:
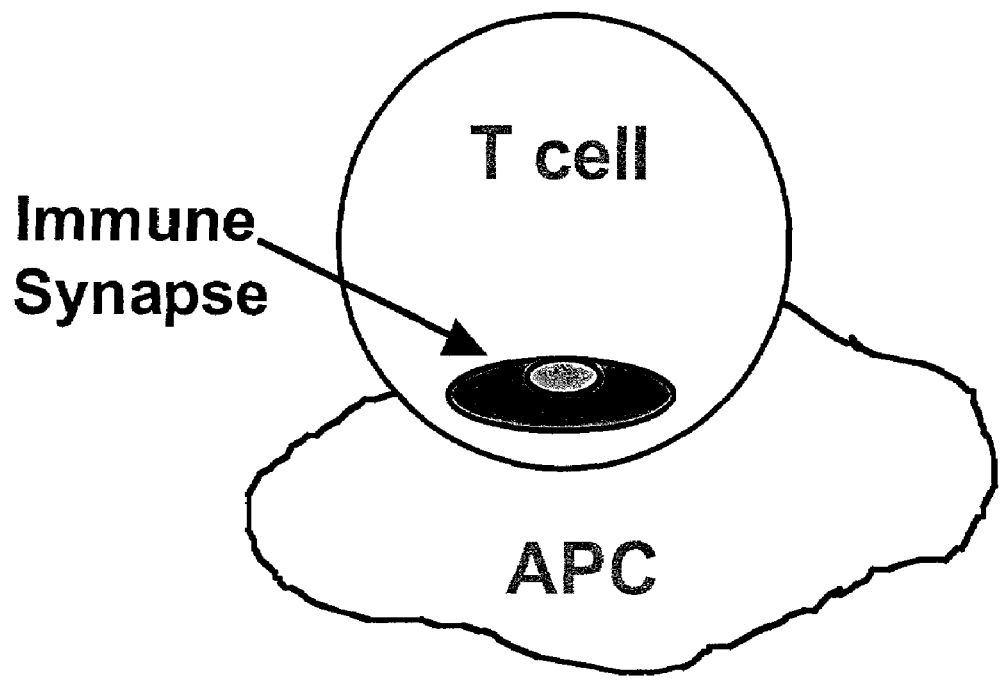
FIG. 1 is a schematic representation of an immune synapse between a T cell and an APC illustrating the doughnut structure of the TCR:peptide:MHC location.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. et al., eds., M. Stockton Press, New York (1991); and Carillo, H., et al. Applied Math., 48:1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLMNIH Bethesda, MD 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, "sequence homology", as used herein, also refers to a method of determining the relatedness of two sequences. To determine sequence homology, two or more sequences are optimally aligned as described above, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A "conservative substitution" refers to the substitution of an amino acid residue or nucleotide with another amino acid residue or nucleotide having similar characteristics or properties including size, charge, hydrophobicity, etc., such that the overall functionality does not change significantly.

"Isolated" means altered "by the hand of man" from its natural state., i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein. Finally, all references and teachings cited herein which have not been expressly incorporated by reference are hereby incorporated by reference.

Sequences including or having a sequence which has at least about 10% sequence identity with any one of SEQ ID Nos. 1-46 and which exhibit similar binding properties to APC or linking properties between two peptide sequences are within the scope of the present invention. Preferably, such sequences will have at least about 30% sequence identity with any one of SEQ ID Nos. 1-46, still more preferably at least about 50% sequence identity, even more preferably, at least about 70% sequence identity, and most preferably at least about 95% sequence identity. Alternatively, sequences including or having a sequence which has at least about 10% sequence homology with any one of SEQ ID Nos. 1-46 and which exhibit similar binding properties to APC or linking properties between the two adjacent peptide sequences are embraced in the present invention. More preferably, such sequences will have at least about 30% sequence homology with any one of SEQ ID Nos. 1-46, still more preferably at least about 50% sequence homology, even more preferably at least about 70% sequence homology, and most preferably at least about 95% sequence homology. Additionally, sequences which differ from any one of SEQ ID Nos. 1-46 due to a mutation event, a series of mutation events, or chemical derivatization but which still exhibit desired properties are also embraced in the present invention. Such mutation events or derivatizations include but are not limited to point mutations, deletions, insertions, rearrangements, peptidomimetics, and other chemical modifications.

A "linker" is defined as any amino acid including naturally occurring or chemically synthesized amino acids. Preferably, a "linker" is a flexible, non-substrate sequence of amino acid residues resistant to proteolytic degradation which can be used to conjugate and/or couple a Signal-1 moiety to a Signal-2 moiety.

A "Signal-1 moiety" is defined as a peptide epitope, i.e., the peptide portion of an antigen and/or mimetics of these antigenic peptides to which important TCRs bind.

A "Signal-2 moiety" or a "Signal-2 receptor moiety" is defined as a peptide portion of a second signal receptor known to bind to and/or affect binding of the receptor to its complimentary ligand on the APC. This can include peptide mimics and mimetics of the receptor/ligand structure of interest.

A "Signal-2 ligand" is the complementary protein of the Signal-2 receptor moiety on the APC to which the receptor portion and/or the Signal-2 receptor moiety has significant affinity and binds.

As used herein "derivative" with respect to peptides refers to changes produced by amino acid addition, deletion, replacement, substitution, and/or modification; mutants produced by recombinant and/or DNA shuffling; and salts, solvates, and other chemically synthesized/modified forms of the peptide that retain in part the activity of the isolated native peptide.

BPI were generated using automated peptide synthesis by a robotic multiple peptide synthesizer employing Fmoc amino acid chemistry by standard methods. Wang resin (p-benzyloxybenzyl alcohol polystyrene) was used as the solid support. Peptides were characterized by reversed-phase HPLC and electrospraymass-spectrometry. This synthesis, referred to as Merrifield peptide synthesis, utilizes traditional organic chemical reactions carried out on a solid material so that the peptide chain is lengthened while attached to the support structure. The peptides will be cleaved from the resin using TFA, and purified by reverse-phase HPLC and analyzed by mass spectroscopy. Alternatively, these reactions can be carried out in solution when larger amounts of the peptides are desired. Of course, the peptides of the invention may be synthesized or prepared by a number of techniques which are well known in the art. See, for example, Creighton, 1983, Proteins: Structures and Molecular Principles, W. H. Freeman and Co., New York, which is incorporated herein by reference in its entirety. Short peptides, for example, can be synthesized on a solid support or in solution. Longer peptides maybe made using recombinant DNA techniques. Here, the nucleotide sequences encoding the peptides of the invention may be synthesized, and/or cloned, and expressed according to techniques well known to those of ordinary skill in the art. See, for example, Sambrook, et al., 1989, Molecular Cloning, A is Laboratory Manual, Vols. 1-3, Cold Spring Harbor Press, New York.

Alternatively, the peptides of the invention may be synthesized such that one or more of the bonds which link the amino acid residues of the peptides are non-peptide bonds. These alternative non-peptide bonds may be formed by utilizing reactions well known to those in the art, and may include, but are not limited to amino, ester, hydrazide, semicarbazide, and azo bonds, to name but a few. In yet another embodiment of the invention, peptides comprising the sequences described above may be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Purchasing preformed peptides provides another alternative source of peptides having 25 amino acids or less as these are easily purchased from commercial peptide synthesis laboratories. In later synthesis schemes, peptide mimetic compounds may be synthesized in place of the peptide moieties and linked by the same chemistry. The design of peptidomimetics is an established technique and known correlates of key amino acids of the peptide can be synthesized by previously published methods. Furthermore, as it is well known in the art, peptidomimetics may be developed which have the same modulation properties as the preferred peptides detailed herein. As these peptidomimetics require no more than routine skill in the art to produce, such peptidomimetics are embraced within the present application. Notably, the side chains of these peptidomimetics will be very similar in structure to the side chains of the preferred peptides herein, however, their peptide backbone may be very different or even entirely dissimilar. If resistance to degradation in vivo or greater conformational stability were desired, the peptides of the present invention could be cyclized by any well known method. One such method adds Penicillamine (Pen) and cysteine (Cys) residues to the N- and C-termini to form cyclic peptides via a disulfide bond between the Pen and Cys residues. The formation of this cyclic peptide restricts the peptide conformation to produce a conformational stability, thereby providing better selectivity for cell surface receptors than its linear counterpart.

The portion of the BPI which spans between the Signal-1 moiety and the Signal-2 moiety is referred to as a linker. As noted above, the linker is not essential in forming a BPI. However, when a linker is used, the linker can be any naturally occurring or chemically synthesized amino acid. Preferably, the linker is a non-substrate amino acid residue chain which helps to prevent protease attack. A particularly preferred linker is a repeating chain of the non-natural amino acid, aminocaproic acid (Ac), and the amino acid glycine (G) (e.g. Ac-G-Ac-G-Ac). If a shorter length was needed for the linker, beta-alanine residues (βAla) could be substituted for one or more of the Ac residues. If a longer chain was needed for the linker, amino-dodecanoic acid residues (Adod) could be substituted for one or more of the Ac residues. As is well known in the art, peptide mimetics of these linker amino acids may also be synthesized and inserted into the BPI structure.

The following examples set forth preferred embodiments of the present invention. It is to be understood, however, that these examples are provided by way of illustration and nothing therein should be taken as a limitation upon the overall scope of the invention.

EXAMPLE 1

This example describes the methods used to generate the BPI.

Materials and Methods:

Synthesis of peptides was via Fmoc on chlorotrity resins. Protected amino acids were double coupled at 8-fold excess for one hour. Resins were dimethylforamide (DMF) and methanol (MeOH) washed and cleaved in Reagent R: trifluorolacetic acid (TFA), ethylene diamine tetraacetic acid (EDTA), Thioanisole, Anisole. The TFA mixture containing the peptide in solution is precipitated in ether and washed extensively. Preparative HPLC of peptides was accomplished by a gradient of 0-80% acetonitrile in 0.1% TFA. Lyophilization of the various fractions and verification by mass spectroscopy yielded the synthetic peptides as a TFA salt. Modeling, crystallography and binding studies are as described above.

Results:

The peptides produced in this example are provided in Table 1 and are also listed as SEQ ID Nos. 1-46. These peptides include the Signal-1 moiety, the Signal-2 moiety and the non-substrate linker between the two moieties. To produce the BPI, any Signal-1 moiety could be linked with any Signal-2 moiety via any linker using the peptide synthesis described above. In other words, the BPI are generated as one continuous peptide chain comprising a Signal-1 peptide sequence followed by a linker sequence followed by a Signal-2 peptide sequence. Additionally, some representative BPI were generated for later use in the experiments. These BPI are included herein in Table 4. However, it is important to note that these BPI are representative (as are each of the BPI portions listed in Tables 1-4) and not all inclusive.

TABLE 1

Signal-1 Peptides

| SEQ ID No. | Sequence | Name, Source | Organism | Health Condition |
|---|---|---|---|---|
| 1 | EIAPVFVLLE | GAD65 (208-217) | Homo sapiens | type-1 diabetes |
| 2 | EIAPVFVLLE | GAD67 (217-226) | Mus musculus | type-1 diabetes |
| 3 | QYMRADQAAGGLR | Collagen II (1168-1180) | Homo sapiens | rheumatoid arthritis |
| 4 | RVVINKDTTIII | Yersinia HSP (322-333) | Yersinia enterocolitica | reactive arthritis |
| 5 | ENPVVHFFKNIVTPR | Myelin BP (84-98) | Homo sapiens | multiple sclerosis |
| 6 | GYKVLVLNPSVAAT | HCV, NS3 (1248-61) | Hepatitis C virus | hepatitis |
| 7 | GSDTITLPCRIKQFINMWQE | HIV, gp120 (410-429) | HIV-1 | AIDS |
| 8 | PIVQNLQGQMVHQAISPRTL | HIV, p24 (133-152) | HIV-1 | AIDS |
| 9 | STPESANL | SIV, Tat (28-35) | Simian immunodeficiency virus | simian AIDS |
| 10 | AICKRIPNKKPGKKT | RSV, G (183-197) | Respiratory syncytial virus | asthma |
| 11 | VYRDGNPYA | HPV 16, E6 (60-68) | Human papillomavirus (HPV) | cervical cancer |
| 12 | DRAHYNI | HPV 16, E7 (48-54) | HPV | cervical cancer |
| 13 | YMLDLQPETT | HPV 16, E7 (11-20) | HPV | cervical cancer |
| 14 | ASDLRTIQQLLMGTV | HPV 33, E7 (73-87) | HPV | cervical cancer |
| 15 | AELYHFLLKYRAR | MAGE (3114-3126) | Homo sapiens | melanoma |
| 16 | LLKYRAREPVTKAE | MAGE (3120-3133) | Homo sapiens | melanoma |
| 17 | EQVAQYKALPVVLENA | Fel d 1 (22-37) | Felis domesticus | cat allergy |
| 18 | KALPVVLENARILKNCV | Fel d 1 (28-44) | Felis domesticus | cat allergy |
| 19 | LVPCAWAGNVCGEKRAYCCS | Amb a 5 (1-20) | Ambrosia artenisiifdia | ragweed allergy |
| 20 | PIGKYCVCYDSKAICNKNCT | Amb t 5 (21-40) | Ambrosia trifida | ragweed allergy |
| 21 | KSMKVTVAFNQFGPN | Cry j 1 (211-225) | Cryptomeria japonica | cedar allergy |
| 22 | IDIFASKNFHLQKNTIGTG | Cry j 2 (182-200) | Cryptomeria japonica | cedar allergy |
| 23 | YFVGKMYFNLIDTKCYK | Phospholypase 2 (81-97) | Apis mellifera | bee allergy |
| 24 | ASEQETADATPEKEEPTAAP | Hev b 5 (37-56) | Hevia brasiliensis | latex |
| 25 | FGISNYCQIYPPNANKI | Der p 1 (111-127) | Dermatophagoides pteronyssinus | dust mites |

TABLE 2

| Linkers | |
|---|---|
| SEQ ID No. | Sequence |
| 26 | Ac-G-Ac-G-Ac |
| 27 | Ac-G-βAla-G-Ac |
| 28 | Ac-G-Adod-G-Ac |
| 29 | Ahx-G-Ahx-G-Ahx |

Discussion:

Once the linker, the Signal-1 moiety, and the Signal-2 moiety are chosen, the entire BPI can be synthesized using the above-described methods. There are thousands of potential Signal-1 moieties which could be used in connection with the present invention. Each of these moieties maybe associated with a distinct immunological response or disease state. Once the epitope structure and sequence are determined, an appropriate linker could be selected and the other portion of the BPI, i.e., the second signal moiety, can be chosen. Once all of these sequences have been determined, BPI can be designed using the peptide sequences themselves, peptidomimetics, or combinations of the two. Construction of appropriate pepti-

TABLE 3

Signal-2 Peptides

| SEQ ID No. | Sequence | Source | Organism | Shift in Immunity |
|---|---|---|---|---|
| 30 | ITDGEATDSG | CD11a (237-247) | *Homo sapiens* | type-1→type-2 |
| 31 | TDGEATDSGN | CD11a (238-248) | *Homo sapiens* | type-1→type-2 |
| 32 | ASPGKATEVR | CTLA4 (24-33) | *Homo sapiens* | type-2→type-1 |
| 33 | SPSHNTDEVR | CTLA4 (24-33) | *Mus musculus* | type-2→type-1 |
| 34 | KVELMYPPPYYL | CTLA4 (93-104) | *Homo sapiens* | type-2→type-1 |
| 35 | KVELMYPPPYFV | CTLA4 (93-104) | *Mus musculus* | type-2→type-1 |
| 36 | ITDGEATDSG | CD11a (237-247) | *Mus musculus* | type-1→type-2 |
| 37 | KGYYTMSNNLVTL | CD154 (CD40L) (93-104) | *Homo sapiens* | type-1→type-2 |
| 38 | KGYYTMSNNLVTL | CD154 (CD40L) (93-104) | *Mus musculus* | type-1→type-2 |
| 39 | YMRNSKYRAGGAYGP G | Fas-ligand (CD95L) (143-155) | *Homo sapiens* | type-2→type-1 |
| 40 | YMRNSKYRAGGAYGP G | Fas-ligand (CD95L) (143-155) | *Mus musculus* | type-2→type-1 |
| 41 | TDGEATDSGN | CD11a (238-248) | *Mus musculus* | type-1→type-2 |

TABLE 4

Some Representative BPI

| TCR Epitope | Linker | Signal-2 Receptor Moiety | Complete BPI Sequence | SEQ ID No. | Effect |
|---|---|---|---|---|---|
| (GAD65) Diabetes: EIAPVFVLLE | AcGAcGAc | (CD11a) ITDGEATDSG | EIAPVFVLLEAcGAcGAcITDGEATDSG | 42 | type-1 → type-2 |
| (tat) AIDS: STPESANL | AcGAdodGAc | (Fas-ligand) YMRNSKYRAGGAYGPG | STPESANLAcGAdodGAcYMRNSKYRAGGAYGPG | 43 | ↑ CTL |
| (p24) PIVQNLQGQMVHQAISPRTL | AcGAcGAc | (CTLA4) KVELMYPPPYFV | PIVQNLQGQMVHQAISPRTLAcGAcGAcKVELMYPPPYFV | 44 | ↑ type-1 |
| (collagen-II) Rheumatoid Arthritis: QYMRADQAAGGLR | AcGAhxGAc | (CD40L) KGYYTMSNNLVTL | QYMRADQAAGGLRAcGAhxGAcKGYYTMSNNLVTL | 45 | type-1 → type-2 |
| (HPVE7) Cervical Cancer: YMLDLQPETT | AcGAcGAc | (Fas-ligand) YMRNSKYRAGGAYGPG | YMLDLQPETTAcGAcGAcYMRNSKYRAGGAYGPG | 46 | ↑ CTL | domimetics is detailed by Falcioni, et al, 17 *Nature Biotechnology*, 562-567 (1999), the content and teachings of which are hereby incorporated by reference herein.

Figure 8:
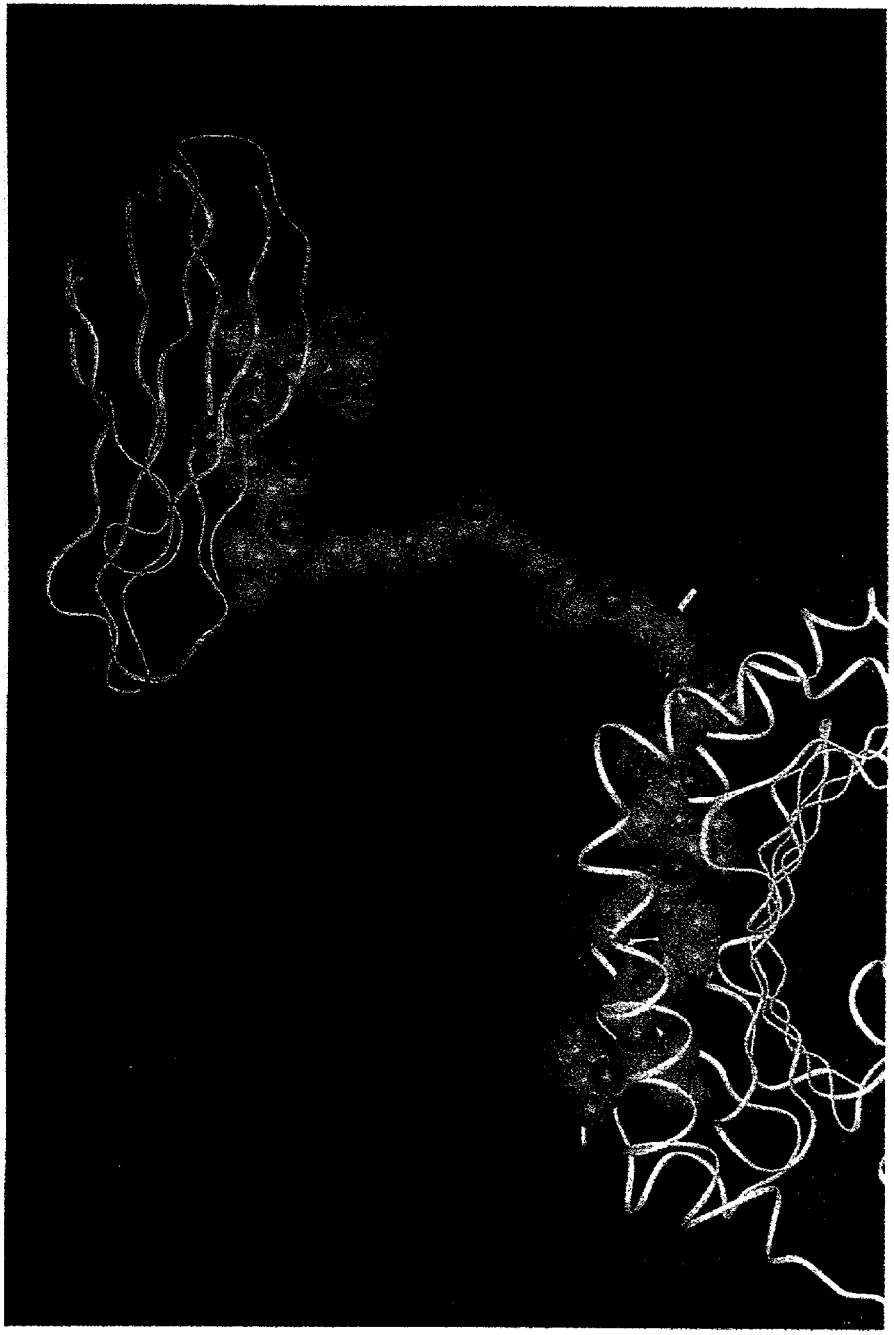
FIG. 8 is a color photograph of the molecular model of a representative BPI binding to the NOD mouse's MHC-II ($I-A^{g7}$) and the D1 domain of ICAM-1, MHC-II is shown in pink, ICAM-1 is in light blue, the BPI is shown by atom with the carbon in green, oxygen in red, and nitrogen in blue.

FIG. 8 illustrates the structure of the GAD65 (208-217), TCR epitope linked to the CD11a (237-247) second signal moiety produced by the present methods. It is shown bound to the groove of I-A$^{g7}$ and the D1 domain of ICAM-1. For modeling the I-A$^{g7}$:GAD65 peptide structure, docking studies were performed on a Silicon Graphic Ocatane work station using InSight II software (MSI/Biosym). The LFA-1 peptide:ICAM-1 domain structure is based on the docking model of Edwards, C. P. et al. *J. Biol. Chem.* 273:28937 (1998), the teachings and disclosure of which is incorporated by reference herein. The alpha carbon ribbon of I-A$^{g7}$ is shown in pink; D1 of ICAM-1 is in light-blue; the BPI is shown by atom, carbon in green, oxygen in red, and nitrogen in blue. This structure can be denominated as GAD65 (208-217)-[Ac-G-Ac-G-Ac]-CD11a (237-247). Advantageously, the length of the linker may be modified as needed or as indicated by any experimental data obtained in order to span between the Signal-1 and Signal-2 moieties at an optimum length.

Figure 2:
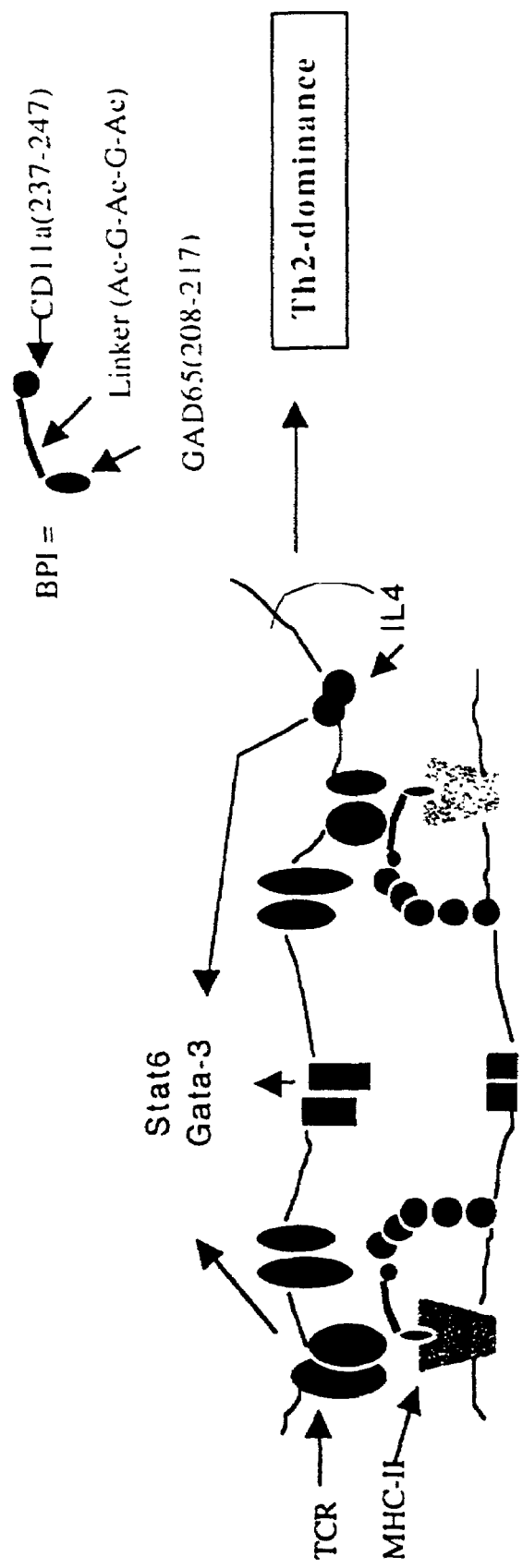
FIG. 2 is a schematic representation of how a representative BPI blocks differentiation leading to a $T_H1$ dominated immune response and shifts immunity to $T_H2$ dominated immune response.
Figure 3:
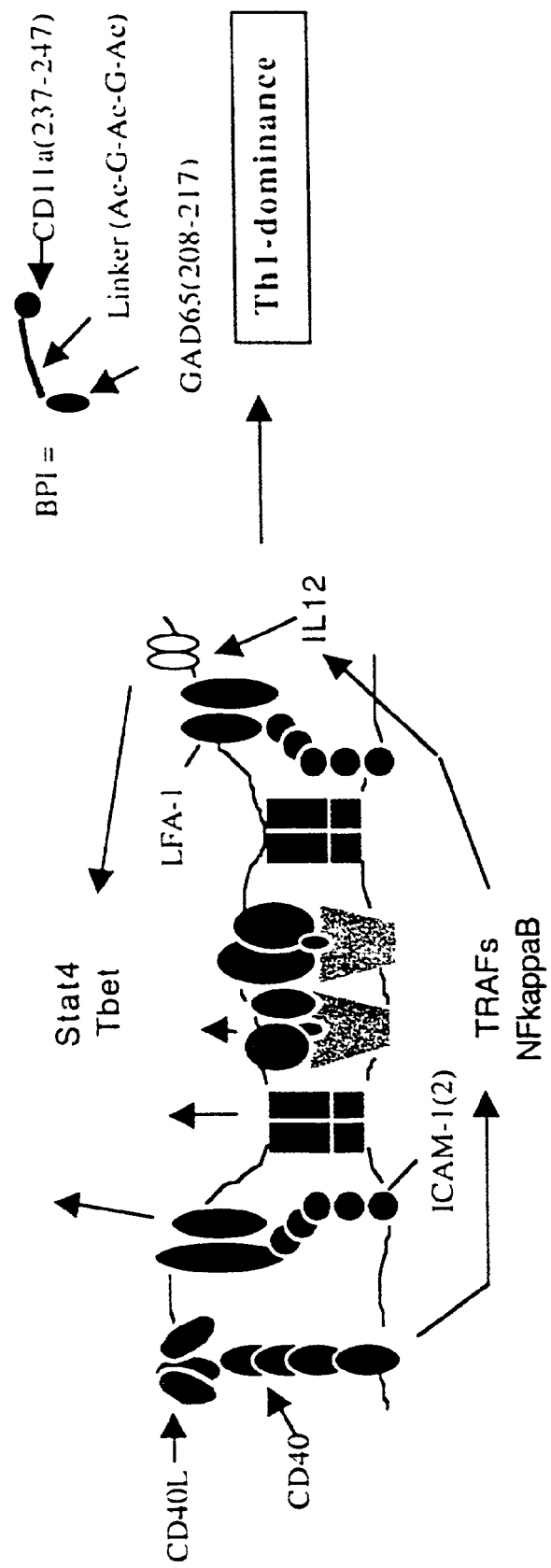
FIG. 3 is a schematic representation of nominal activation of a type-1 immune response through the interactions between cell surface proteins within the immune synapse.
Figure 4:
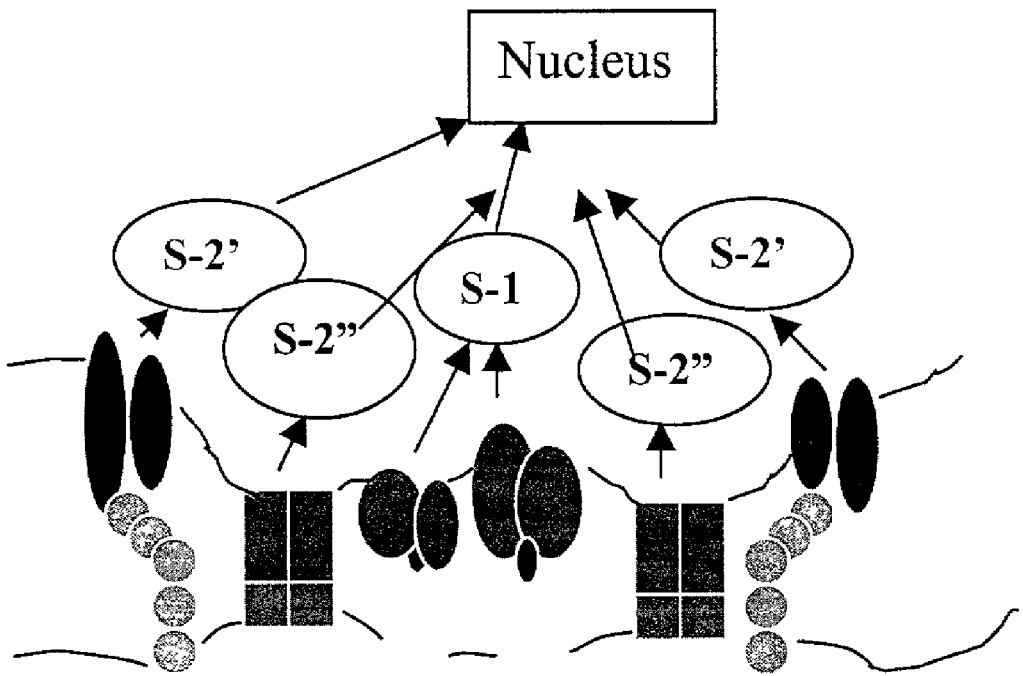
FIG. 4 is a simplified schematic representation of the two signal mechanism of T-cell activation.

These structures are illustrated by the preliminary mechanism depicted schematically (FIGS. 2 and 3), and the structural model (FIG. 8). The linker used has the sequence-[Ac-G-Ac-G-Ac]-. To lengthen the linker, one or more aminocaproic acid (Ac) resides can be substituted with aminododecanoic acid. To shorten the linker, beta-2 alanine can be used as a substitute for aminocaproic acid.

Of course, it is possible that one of ordinary skill in the art could produce any number of peptidomimetics or derivatives which would have similar activity to the BPI, and such modifications are encompassed by the present invention as described in more detail above.

EXAMPLE 2

This example uses biotinylated BPI to test for competitive inhibition of BPI binding by unlabeled peptides or monoclonal antibodies to MHC-II and ICAM-1 on live APC, and to verify antigenic peptide binding to live APC. Additionally, it was shown that monoclonal antibodies to MHC-II or ICAM-1 effectively block binding of the diabetes BPI (GAD65(208-217)-[Ac-G-Ac-G-Ac]-CD11a (237-247)) (hereinafter referred to as EGAD-BPI) to NOD spleenocytes.

Materials and Methods:

To obtain biotinylated BPI, the synthesized EGAD BPI was biotinylated with NHS-Biotin as described in Murray et al., 24 *Eur. J. Immunol.* 2337-2344 (1994). Spleen cell density-gradient fractions from normal (unimmunized) NOD, BALB/c and other MHC congenic strains were incubated in round bottom 96-well plates with increasing concentrations of individual biotinylated peptides at 37° C., 5% $CO_2$ for 16 hours. Following binding of the BPI to the APC, Avidin-FITC was incubated with the cells on ice for 30 minutes, followed by biotinylated anti-Avidin for 1 hour, then again with Avidin-FITC. For BPI titrations, increasing concentrations (0.1-100 µM) of the biotinylated derivatives in sterile 0.5% BSA-PBS were incubated with the APC for 16 hours as above. Three-color analyses used Cy-Chrome or PE-conjugated anti-B220 (mAb RA3-6B2 (CD45R B-cell marker), anti-MHC class II (KH74 or 10-3.62 mAb), or anti-ICAM-1 (3E2 mAb); (all purchased from PharMingen, San Diego, Calif.). Bound peptide was detected with avidin-FITC/biotinylated anti-avidin/avidin-FITC on live cells gated by forward/side scatter analysis. Controls contained all detecting reagents in absence of the biotinylated peptide; 20,000 events were analyzed for each histogram with a FACScan (Becton-Dickinson) flow cytometer.

To test for competitive inhibition of BPI binding with unlabeled peptides or monoclonal antibodies to MHC-II and ICAM-1 on live APC, freshly isolated fractions of spleen cells were incubated with the previously biotinylated BPI. However, for this portion of the experiment, the experimental wells contained various unlabeled peptides (e.g., antigenic peptides or LFA-1 peptides), and/or monoclonal antibody (e.g., anti-MHC-II or anti-ICAM-1 mAb) inhibitors. Negative selection methods with monoclonal antibodies conjugated to magnetic particles were used to enrich the spleen cell fractions for B cells, macrophages, or dendritic cells as well as to examine differences in BPI binding to these different populations. These methods are detailed in Schountz et al., 157 The Journal of Immunology 3893-3901 (1996), the teachings and content of which were incorporated by reference above.

To verify antigenic peptide binding to live APC, initial EGAD-BPI were screened for selective binding to NOD (I-A$^{g7}$) APC and assayed for simultaneous binding using monoclonal antibodies against either MHC-II or ICAM-1 by flow cytometry methods using live APC (Murray et al., 24 *Eur. J. Immunol.* 2337-2344 (1994); Murray; 19 *Immunology Today* 157-163; and Schountz et al., 157 *The Journal of Immunology* 3893-3901 (1996)). In this assay, increasing concentrations of the biotinylated-BPI, -CD11a(237-247) or -GAD65(208-217) peptide were incubated overnight with spleenocytes from each inbred strain. Bound peptide was detected with amplification of avidin-FITC fluorescence by the use of a biotinylated anti-avidin reagent, followed by a second round of avidin-FITC binding. Biotinylated peptide was incubated with $10^6$ viable cells at a peptide concentrations of 50 µM. Bound peptide was detected with avidin-FITC/biotinylated anti-avidin-FITC. For analysis, a forward/side scatter gate was set on live lymphocytes and 20,000 events were collected in this gate. Background fluorescence (detection reagents only) is shown in each panel of FIGS. 5a-5c along with the 50 µM bio-peptide histogram (peptide-fluorescence intensity=FL1). The percentage of positive cells (M2) were determined by the CELLQuest™ program (Becton-Dickinson) and are displayed in each panel along with the median channel fluorescence (MCF) of the M2 population (all data are the direct output of the CELLQuest™ program running on an Apple G3 computer).

Figure 5A:
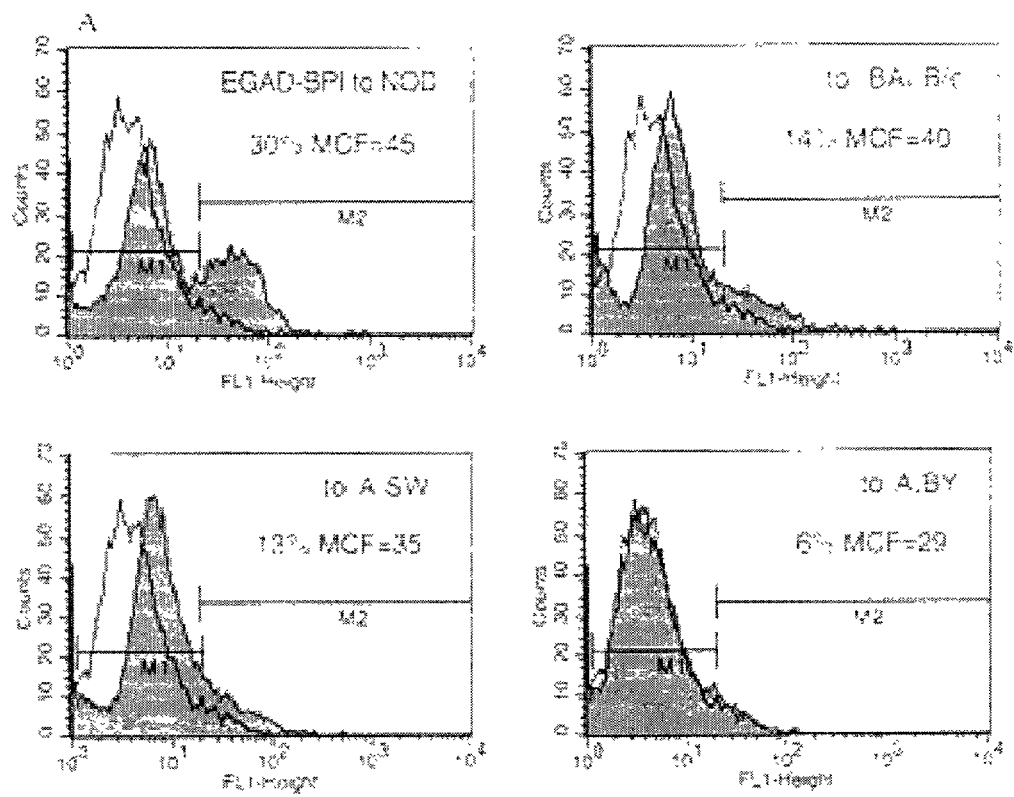
FIG. 5a is a graph representing the results of a flow cytometry analysis comparing the binding of a representative BPI to different mouse strains.
Figure 5B:
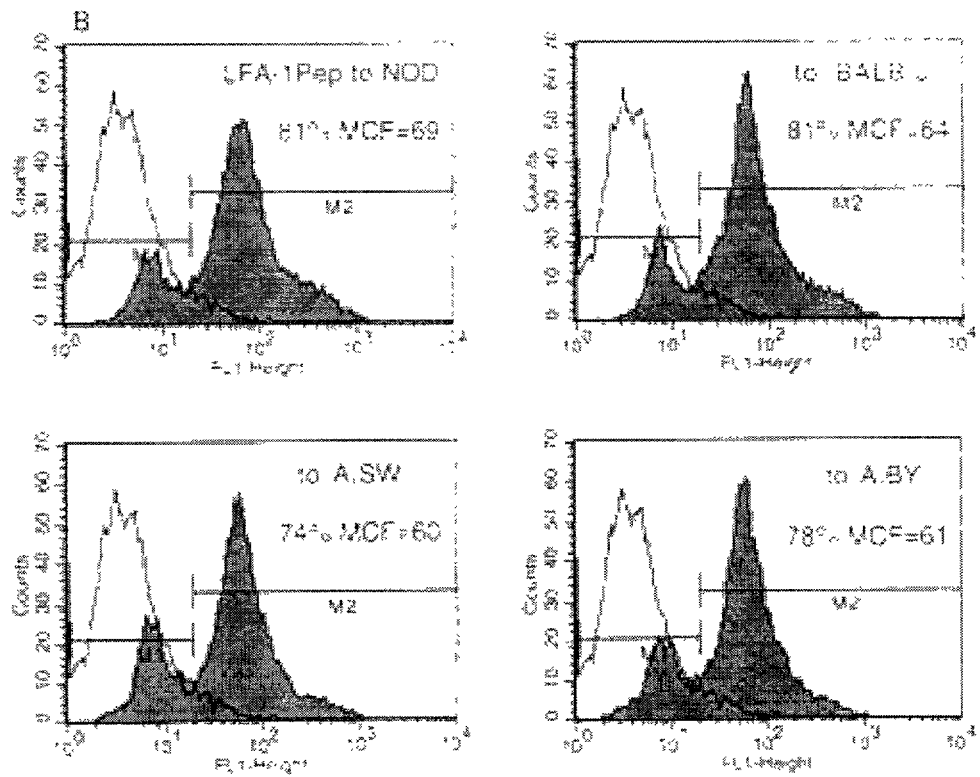
FIG. 5b is a graph representing the results of a flow cytometry analysis comparing the binding of a representative BPI portion to different mouse strains.
Figure 5C:
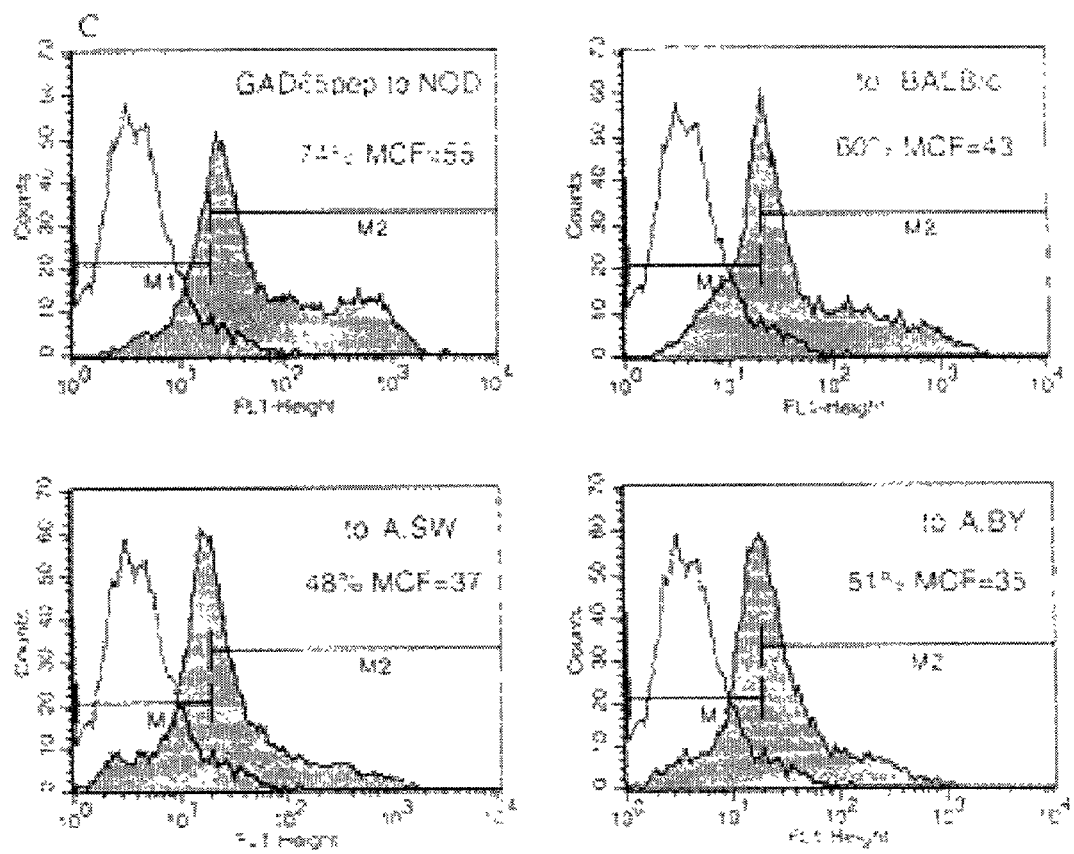
FIG. 5c is a graph representing the results of a flow cytometry analysis comparing the binding of a representative BPI portion to different mouse strains.

To demonstrate that monoclonal antibodies to MHC-II or ICAM-1 effectively block binding of the diabetes BPI (EGAD-BPI) to NOD spleenocytes, an assay identical to that used for FIGS. 5a-5c was used. However, either purified 10-3.62 (anti-MHC-II) or 3E2 (anti-ICAM-1) were included in the overnight incubation of the spleen cells with the biotinylated BPI. Both antibodies were purchased from PharMingen and used at 5 µg/ml final concentration. A control containing no added monoclonal antibody was also tested. Analyses were gated on forward/side scatter dotplots for live lymphocytes and 20,000 events were analyzed for each histogram. Results for this example are given in FIGS. 6a-6c.

Results and Discussion:

As illustrated by the data provided in FIGS. 5a-5c, NOD spleen cells bind the diabetes BPI (EGAD-BPI) at a higher density than spleenocytes identically purified from BALB/c, A.SW, or A.BY. Previous data has shown that B cells are the major antigenic peptide binding cells in these spleen cell preparations isolated by lymphocyte separation media (LSM) density gradient centrifugation (Murray et al., 24 *Eur. J.*

*Immunol.* 2337-2344 (1994); Murray; 19 *Immunology Today* 157-163; and Schountz et al., 157 *The Journal of Immunology* 3893-3901 (1996)). There was a significant difference in the percentage of high-density binding cells, from 30% (NOD) to 6% (A.BY). In contrast, the separate Signal-1 (GAD65 peptide) and Signal-2 (CD11a peptide) moieties did not bind preferentially to NOD APC. Supporting data is given in FIGS. 5*b* and 5*c*. FIG. 5*b* illustrates direct binding of biotinylated LFA-1 (CD11a 237-247) peptide to the same spleenocyte preparations as those shown in FIG. 5*a*. Note that this Signal-2 moiety bound similarly to all strain spleenocytes. FIG. 5*c* illustrates direct binding of biotinylated GAD65 (208-217) peptide to the same spleenocyte preparations as those depicted in FIGS. 5*a* and 5*b*. These data indicate that BPI could be engineered to fit particular MHC peptide binding motifs as discussed by Corper et al. in *A Structural Framework for Deciphering the Link Between I-A$^{g7}$ and Autoimmune Diabetes*, 288 Science 505-511 (2000), and by Dessen et al. in *X-ray Crystal Structure of HLA-DR4 (DRA\*0101, DRB\*0401) Complexed With a Peptide From Human Collagen II*, 7 Immunity 473-481 (1997), the respective teachings of which are incorporated by reference herein.

Figure 6A:
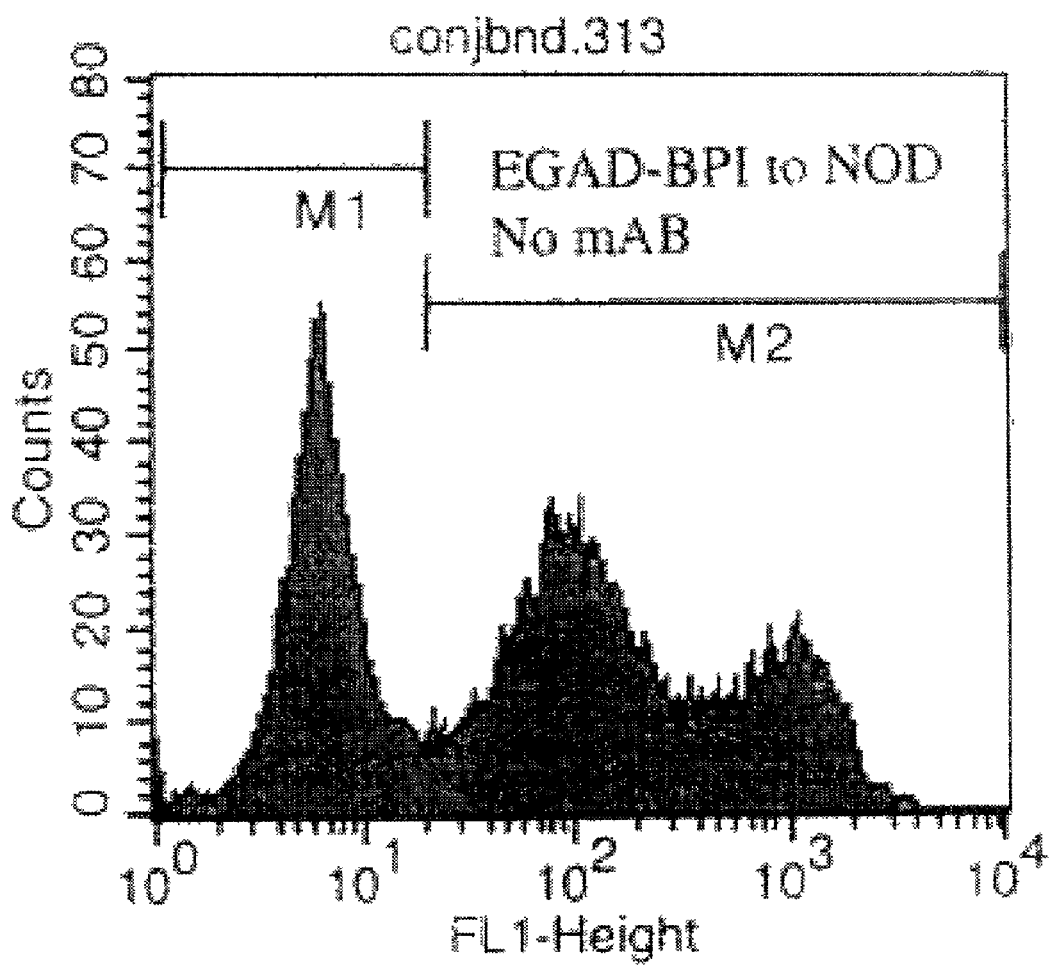
FIG. 6a is a graph illustrating the results of a flow cytometry analysis of a representative BPI binding to the APC of a mouse strain, without antibodies to MHC-II or ICAM-1.
Figure 6B:
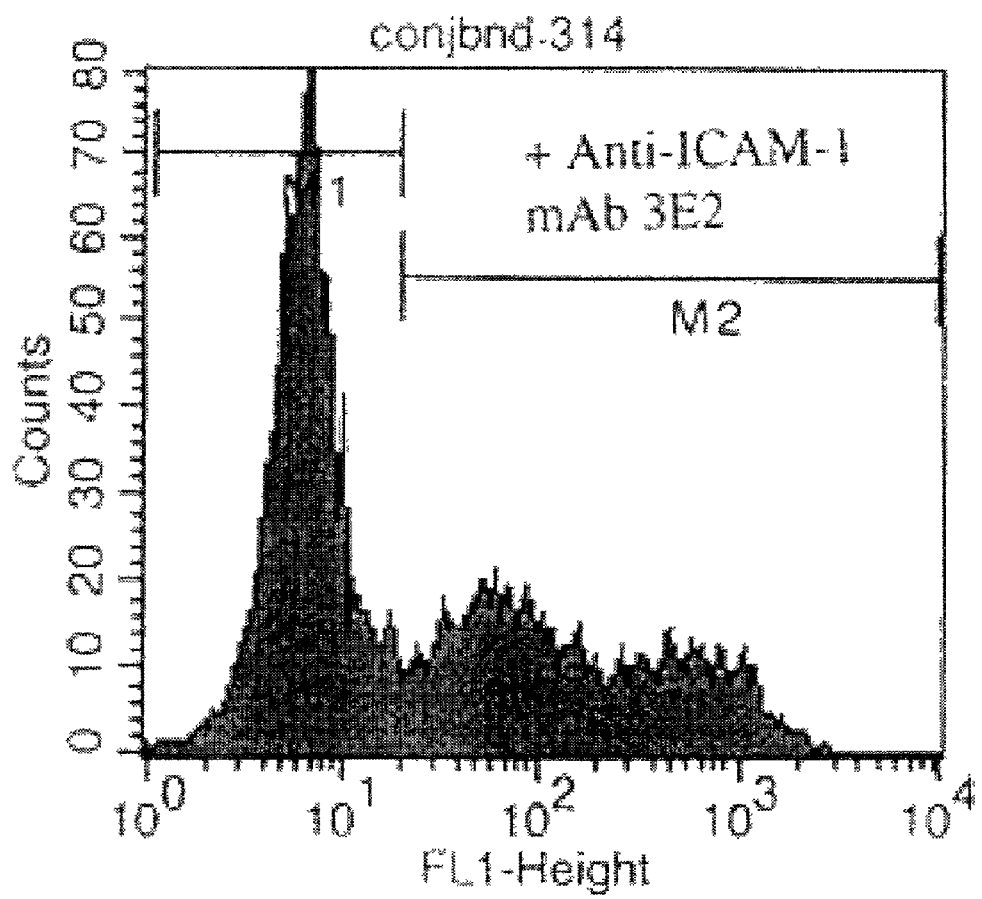
FIG. 6b is a graph illustrating the results of a flow cytometry analysis of a representative BPI binding to the APC of a mouse strain, when antibodies to ICAM-1 are present.
Figure 6C:
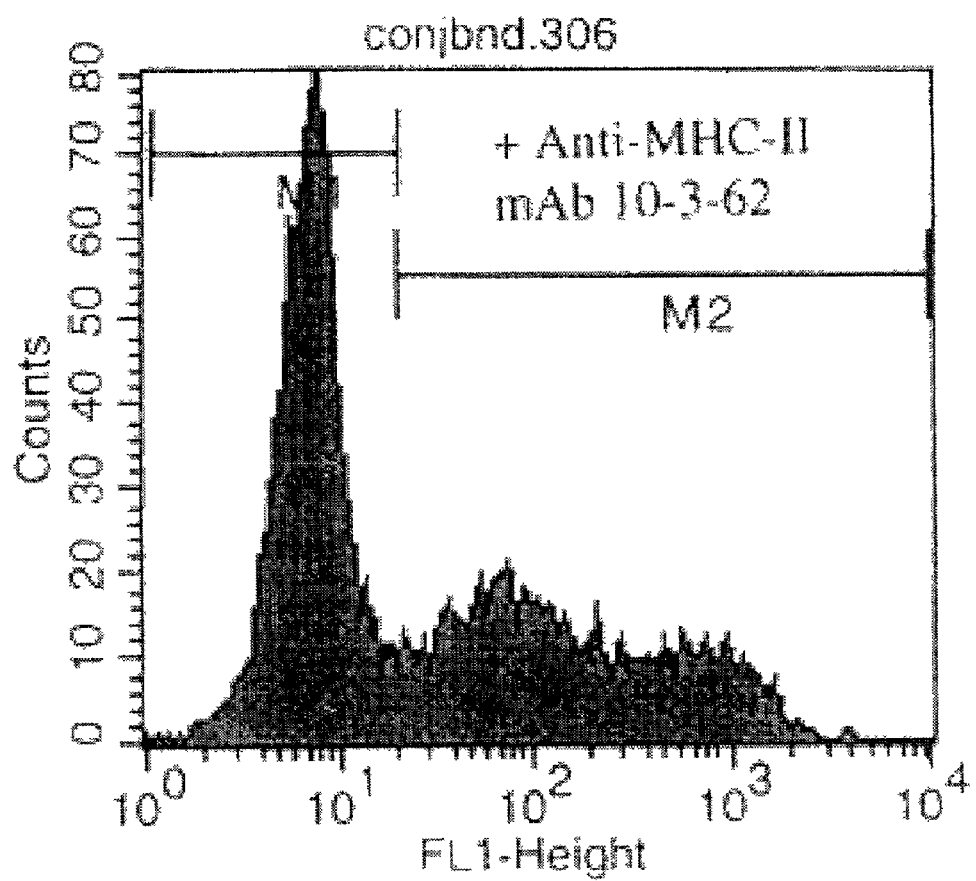
FIG. 6c is a graph illustrating the results of a flow cytometry analysis of a representative BPI binding to the APC of a mouse strain, when antibodies to MHC-II are present.

Additionally, as illustrated in FIGS. 6*a*-6*c*, other studies have shown that monoclonal antibodies to MHC-II and ICAM-1 block peptide binding to NOD spleen cells. These data indicate that the diabetes BPI bind to both receptors on the APC surface. Thus, Monoclonal antibody to MHC-II or ICAM-1 effectively block binding of the diabetes BPI (EGAD-BPI) to NOD spleenocytes. In effect the predicted bifunctional nature of the BPI is demonstrated by these results and suggests that the BPI will link MHC-II to ICAM-1 on the APC surface. This mechanism was further demonstrated by co-capping experiments.

EXAMPLE 3

This example utilizes co-capping experiments to demonstrate simultaneous binding of the BPI to MHC-II and ICAM-1 molecules.

Materials and Methods:

Further support for simultaneous binding of the BPI to MHC-II and ICAM-1 molecules has been observed in co-capping experiments using biotinylated mAb 10-3.62 and streptavidin to cap MHC-II in the presence or absence of the BPI. To test the ability of the BPI peptide to link MHC-II and ICAM-1 molecules on the APC surface, we used a modification of a co-capping experiment originally described for monoclonal antibodies. Briefly, biotinylated monoclonal antibody to MHC-II (10-3.62) is incubated with freshly-isolated APC from NOD mice previously treated by intravenous (i.v.) injection of a given BPI variant or saline. Antibody-bound cells are then incubated with streptavidin (37 C×15 min.) to cap the MHC-II molecules on the APC surface. The cells were transferred to ice and labeled with a fluorescent (PE) monoclonal antibody to ICAM-1 (3E2). The cells are plated and observed for evidence that a given BPI links ICAM-1 into the MHC-II cap, i.e., by standard fluorescence microscopy and image analysis. In one experiment, T-depleted spleenocytes from mice treated 16 hours previously with EGAD-BPI (i.v.) exhibited co-capping of ICAM-1 with MUC-II in the presence of bio-10-3.62/streptavidin. In the other experiment, T-depleted spleenocytes from mice treated 16 hours previously with saline only did not exhibit co-capping. The results for these experiments are given in FIG. 7.

Figure 7:
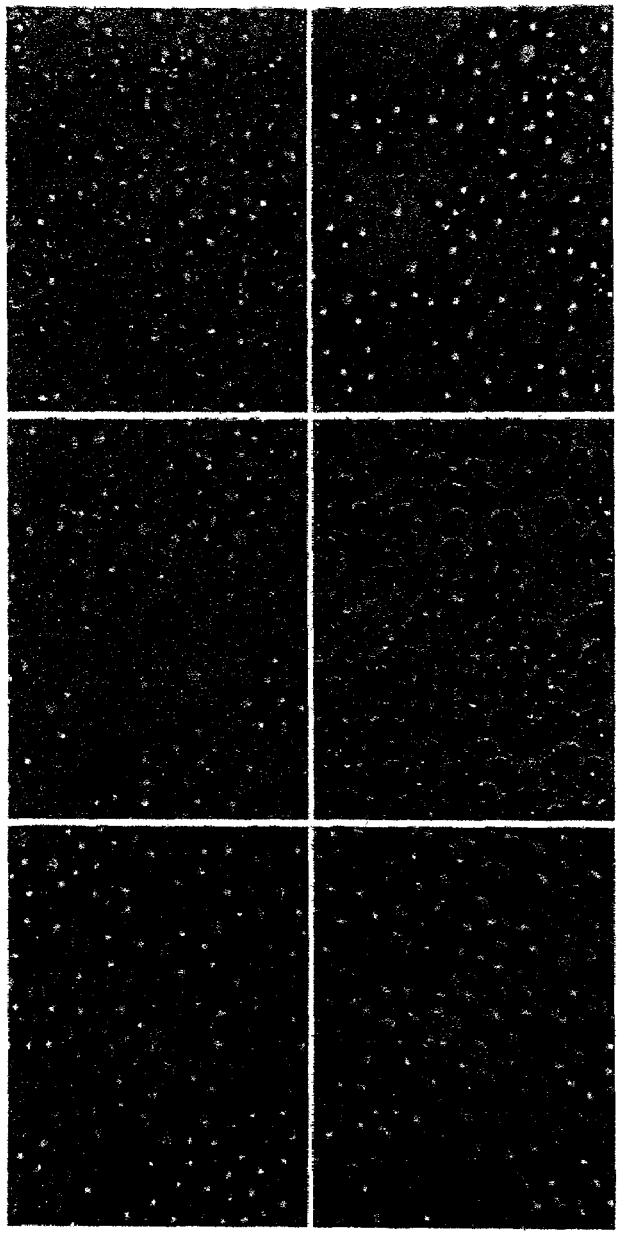
FIG. 7 is a color photograph representing the results of a fluorescent microscopy analysis of a representative BPI simultaneously binding to MHC-II and ICAM-1 structures on the NOD APC by co-capping with antibodies to MHC-II, the top panels are from mice APC treated with a representative BPI and the bottom panels are treated with just the saline vehicle.

Results:

The top panels of FIG. 7 illustrate the results from the T-depleted spleenocytes from mice treated 16 hours previously with EGAD-BPI (i.v.), wherein ICAM-1 was co-capped with MHC-II in the presence of bio-10-3.62/streptavidin. The bottom panels of FIG. 7 illustrate the results from the mice treated with saline only wherein co-capping is not exhibited. This is evidenced by having ICAM-1 remain dispersed on the B-cell membranes. As is shown, B cells isolated from NOD mice treated 16 hours previously by i.v. injection of either 40 nanomoles of EGAD-BPI or saline (PBS) alone displayed two distinct patterns of ICAM-1 expression, as measured by staining with PE-labeled 3E2 (anti-ICAM-1) on ice. On cells from BPI-treated mice, ICAM-1 appears to have co-capped with the MHC-II molecules (note single concentrated spot of ICAM-1 red fluorescence in top panels). By contrast, the nominal dispersed density of ICAM-1 is observed on cells isolated from PBS-treated NOD mice (note entire surface red fluorescence staining in bottom panels).

Therefore, it appears evident that BPI have the capacity to bind simultaneously to MHC-II and ICAM-1 structures on the surface of live APC and therefore may provide signal alterations involving pathways necessary for $T_H1/T_H2$ differentiation. To directly examine the effects of BPI on $T_H1/T_H2$ immune deviation, T-cells from mice injected with EGAD-BPI were examined for cytokine analysis.

EXAMPLE 4

This example used an ELISPOT to determine $T_H1/T_H2$ frequency as altered by BPI injection.

Materials and Methods:

Groups of 3-5 NOD mice were immunized subcutaneously (s.c.) with the GAD 65 peptide in CFA (40 nanomoles/mouse) at the tail base. Different groups received either the EGAD-BPI, its single TCR epitope (Signal-1 moiety), or its CD11a peptide (Signal-2 moiety) i.v. (all 40 nanomoles/mouse). After 6-8 days, another identical 40 nanomole injection was given to each mouse, and the next day lymph nodes draining the site of the s.c. injection were made into single cell suspensions for culture. Identical primary cultures were incubated for 96 hours; then, viable T-cells were recovered by density gradient centrifugation. One million of these cells were combined in nitrocellulose-bottomed 96-well plates (Millititer-HA, Millipore, Bedford, Mass.), previously coated (50 µl/well) with mAb to either mouse IFNγ (clone R4-6A2), or mouse IL-4 (clone BVD4-1D11) at a concentration of 10 µg/ml in PBS. Groups of triplicate cultures were incubated with either Concanavalin-A (2 µg/ml), or the Signal-1 peptide moiety plus 20 U/ml recombinant IL2 (R & D Systems). After 72-96 hours of culture at 37° C. and 5% $CO_2$, plates were washed three times with PBS-0.05% Tween-20. In appropriate wells are added biotinylated anti-IFNγ (clone XMG1.2) or biotinylated anti-IL-4 (clone BVD6-24G2) at a concentration of 1 µg/ml and incubated for 1 hour at room temperature. Positive control wells receive known $T_H1$ or $T_H2$ clones in place of normal T-cells. MAb pairs to IL12, IL10, and IL2 are also available and will be used to test for these cytokines in the same assay. All mAb and recombinant controls are purchased from PharMingen (San Diego, Calif.). Finally, plates were washed three times with PBS-Tween, and then exposed to 100 µl of a 1:2000 dilution of streptavidin alkaline phosphatase (Jackson ImmunoResearch, West Grove, Pa.) for 1 h and washed as before. Cytokine-producing cells were enumerated by development of the membrane with BCIP/NBT substrate kit (BioRad Labs, Richmond, Calif.), followed by image capture and analysis using a standard stereomicroscope connected with a digital camera and NIH image software (Murray et al., 24 Eur. J. Immunol. 2337-2344 (1994); Murray; 19 Immunology Today 157-163; and Schountz et al., 157 The Journal of Immunology 3893-3901 (1996)). In separate experiments, CD4+ T-cell clones from NOD mice immunized with the GAD65(208-217) peptide by our previously described methods can be used in the same assay. The clones were generated using the methods described in Murray et al., 24 Eur. J. Inmunol. 2337-2344 (1994), the teachings of which are hereby incorporated by reference. These clones will be maintained by biweekly restimulation with irradiated NOD lymphocytes, the GAD peptide, and recombinant IL-2. For further analysis, BPI that have been substituted at predicted TCR-contact positions will be used to determine which of these BPI variants are most effective in the inhibition of proliferation and cytokine release from individual clones as analyzed above. Predicted positions that will be scanned with all amino acids except cysteine are amino acids 208, 213, and 216. These residues point toward the TCR in the recently solved crystal structure of the GAD65 peptide bound to I-A$^{g7}$ (Corper et al., 288 Science 505-511 (2000) and see FIG. 8).

Results:

Importantly, this example shows the ability of a given BPI to modulate a functional immune response. It can be seen that mice treated with the BPI produce abundant IL-4, whereas the control mice did not produce this cytokine (illustrated in FIGS. 9a and 9c). Since IL-4 is the signature cytokine of type-2 immunity, this example shows that the BPI have the capacity to switch dominant type-1 immunity toward $T_H2$ differentiation and a type-2 response. Moreover, we have developed this in vivo assay system to provide a relatively quick examination of a given BPI's immunoregulatory efficacy. Once $T_H1/T_H2$ modulation is confirmed as in the present example, studies can then move on to the more stringent tests of BPI efficacy using adoptive transfer experiments as described below.

Figure 9A:
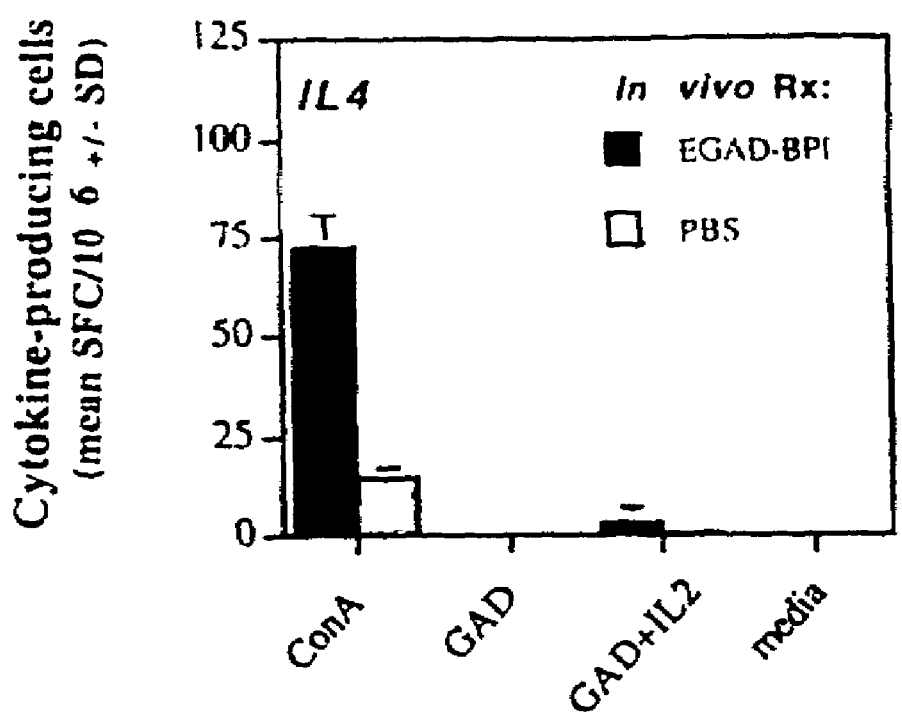
FIG. 9a is a graph representing the ELISPOT analysis of IL-4 cytokine release by T-cells taken from NOD mice treated with the EGAD-BPI or the saline control.
Figure 9B:
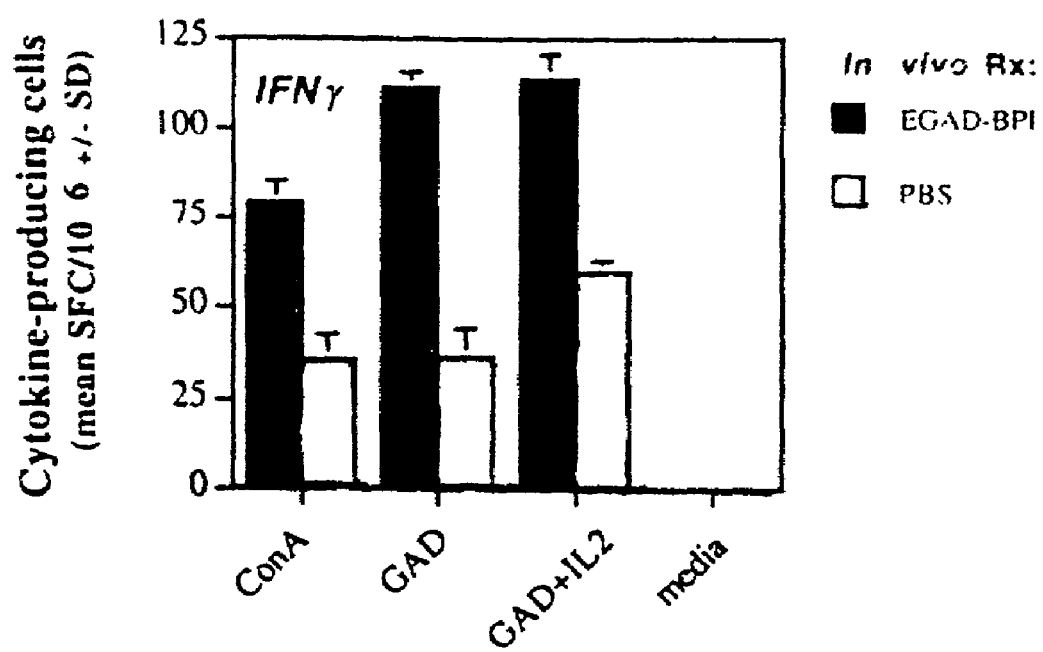
FIG. 9b is a graph representing the ELISPOT analysis of IFN-γ cytokine release by T-cells taken from NOD mice treated with the EGAD-BPI or the saline control.
Figure 9C:
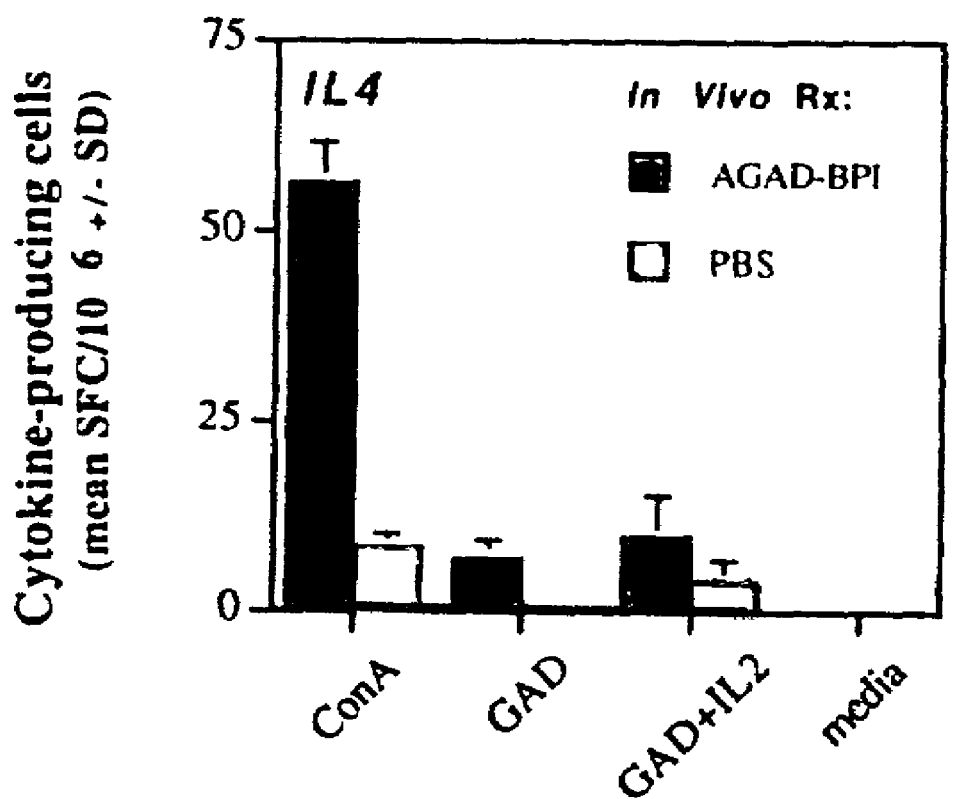
FIG. 9c is a graph representing the ELISPOT analysis of IL-4 cytokine release by T-cells taken from NOD mice treated with the AGAD-BPI or the saline control.
Figure 9D:
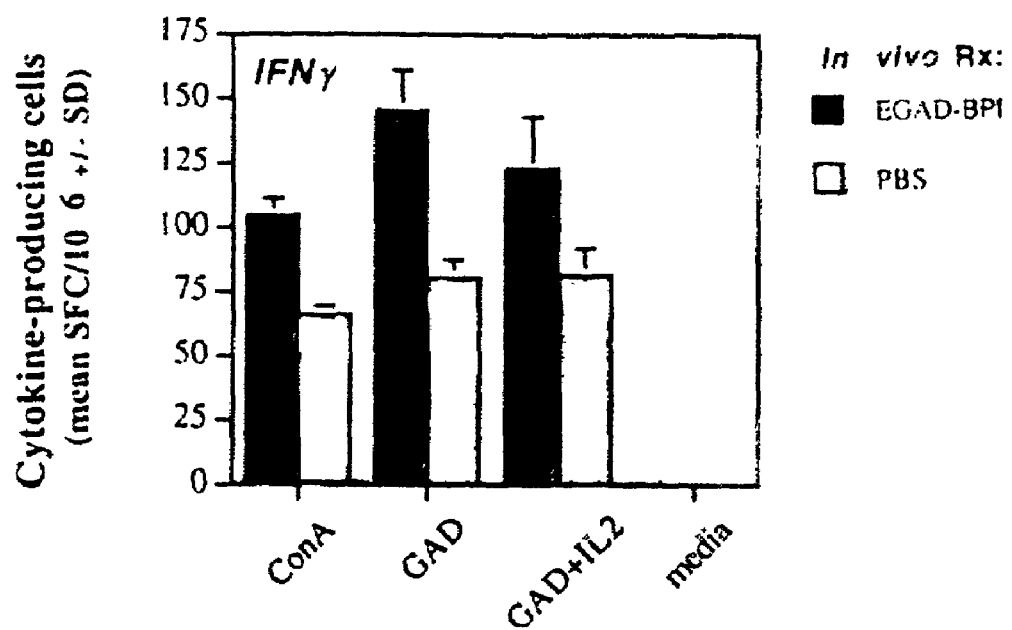
FIG. 9d is a graph representing the ELISPOT analysis of IFN-γ cytokine release by T-cells taken from NOD mice treated with the AGAD-BPI or the saline control.
Figure 10:
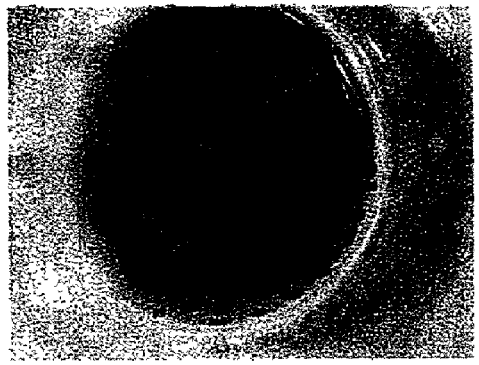
FIG. 10 are representative photographs of the raw data of the ELISPOT analysis used for the graphs in FIGS. 9a-9d.
Figure 10:
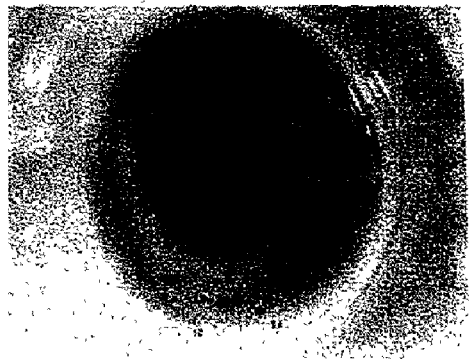

As shown in FIGS. 9a and 9c, IL-4 production increases by approximately 10-fold when T-cells are from the BPI treated animals stimulated in vitro with mitogen. IFN-γ production also increased, although to a lesser extent (see FIGS. 9b and 9d).

EXAMPLE 5

This example tested the capacity of the BPI to inhibit lymphocytic infiltration of pancreatic islets in NOD mice. Lymphocytic infiltration is a hallmark of insulitis and the development of type-1 diabetes.

Materials and Methods:

These studies sought to confirm that the BPI containing the immunodominant GAD65 TCR epitope (EGAD-BPI) was biologically active in vivo and inhibited the development of pancreatic inflammation. Groups of three normal glycemic NOD males (8 weeks old) were immunized with the GAD65 (208-217) peptide in CFA as described in Example 4. The control group received PBS, and separate experimental groups received either the EGAD-BPI, the GAD peptide alone (i.e., the T-cell receptor epitope), or the CD11a peptide alone(i.e., the second signal receptor moiety) by two intravenous injections as described in Example 4. On day 10, the pancreata were removed to 10% PBS-buffered formalin, embedded in paraffin, and five-micron serial sections were examined histologically for mononuclear cell infiltration as previously described by Yoon, et al., Control of Autoimmune Diabetes in NOD Mice by GAD Expression or Suppression in β Cells, 284 Science 1183-1187 (1999), the entirety of which is hereby incorporated by reference.

Figure 11:
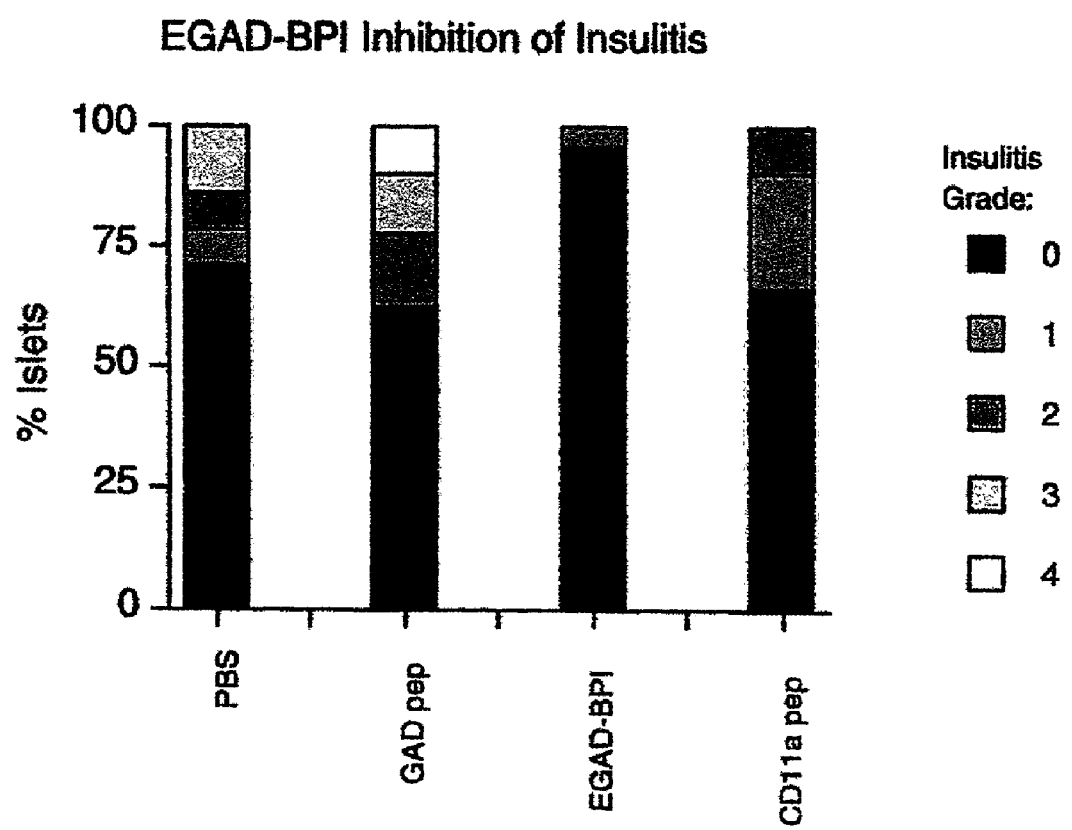
FIG. 11 is a graph of the severity of islet infiltration as an indicator of the inhibition of insulitis by the EGAD-BPI, separate portions of the EGAD-BPI, and saline.
Figure 12A:
FIG. 12a is a representative color photograph of the histological analysis of pancreata infiltration by mononuclear cells in NOD mice treated with the saline control.
Figure 12B:
FIG. 12b is a representative color photograph of the histological analysis of pancreata infiltration by mononuclear cells in NOD mice treated with the GAD peptide.
Figure 12C:
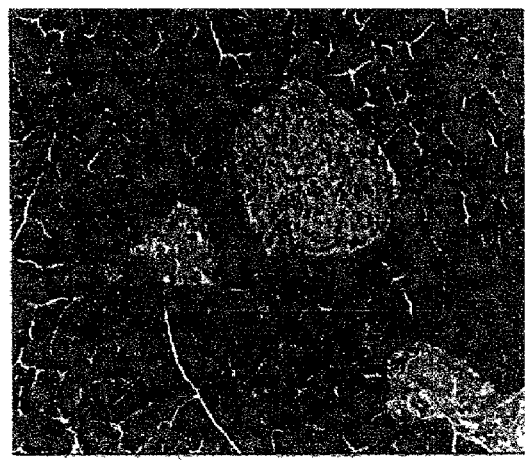
FIG. 12c is a representative color photograph of the histological analysis of pancreata infiltration by mononuclear cells in NOD mice treated with the EGAD-BPI.
Figure 12D:
FIG. 12d is a representative color photograph of the histological analysis of pancreata infiltration by mononuclear cells in NOD mice treated with the CD11a peptide.

Results:

The results for this experiment are given in FIGS. 11 and 12. FIG. 11 represents the cumulative data of this analysis wherein the severity of islet infiltration is scored and plotted as the percentage of islets examined. Over 100 islets from each group in greater than 5 tissue sections were analyzed by three independent observers. As shown in FIG. 11, there was a clear inhibitory effect of the EGAD-BPI treatment on mononuclear cell infiltration (insulitis). Over 95% of the islets from the BPI treated animals were intact and did not show infiltration (i.e., grade-0 islets). All of the other groups showed some signs of insulitis even at this early stage of the disease. Notably, the GAD peptide treated animals showed the most insulitis (grade-0 islets reduced to 62% and 37.5% of islets scored grade 2 or above. This compared with 66.7% normal islets in the CD11a peptide treated group and 71.4% normal islets in PBS treated animals. Thus, compared to the PBS control, EGAD-BPI treatment provided an 84% inhibition of insulitis [calc. as: % islets @grade 1-4 (PBS Rx) minus % islets @grade 1-4 (EGAD-BPI Rx) divided by % islets @grade 1-4 (PBS Rx) multiplied by 100]. Representative islets from each group of the experiment are shown below in FIGS. 12a-12d, as stained with hematoxylin and eosin. Note severe lymphocytic infiltration in FIGS. 12b and 12d which was observed in groups treated with the single Signal-1 or Signal-2 moieties while the islets from the EGAD-BPI treated mice were predominately intact (see FIG. 12c). Taken together, these data strongly indicate that treatment with the diabetes BPI containing these Signal-1 and Signal-2 peptide moieties significantly inhibits the infiltration of lymphocytes into the pancreatic islets in this animal model of type-1 diabetes. Therefore, we would predict that BPI operate via a mechanism involved in the normal breakdown of self tolerance to pancreatic autoantigens. These data indicate that BPI may operate through immune deviation to block the autoimmune response to pancreatic antigen. To further test this theory, we transferred T-cells primed in the presence of the EGAD-BPI into NOD.Scid mice genetically programmed for diabetes development.

EXAMPLE 6

This example tested BPI blocking of diabetes development in the well described intact immune system of immunologically reconstituted NOD.Scid mice to study diabetes progression.

Materials and Methods:

BPI proven active for modulation of $T_H1/T_H2$ responses against known immunodominant peptides of GAD65 for blocking T-cell initiated diabetes progression in a NOD mouse model was tested. The NOD.Scid adoptive transfer model, wherein CD25-depleted NOD spleen cells have been observed to induce diabetes as early as 2-4 weeks post adoptive transfer was used for this purpose. NOD.Scid adoptive transfers were performed by a modification of a protocol described by Solomon et al. in B7/CD28 Costimulation is Essential for the Homeostasis of the CD4$^+$ CD25 Immunoregulatory T-cells That Control Autoimmune Diabetes, 12 Immunity 431-440 (2000), the content of which is incorporated herein by reference. NOD spleen cells from 8 week (non-diabetic) females were used to enrich a CD25-/CTLA4-depleted population by treatment with purified monoclonal antibody (mAb 7D4, PharMingen) followed by low-tox rabbit complement (Cedarlane) (80% depletion of CTLA4+ cells by flow analysis with PE-labeled UC10-4F10-11 mAb; not shown). These inducer cells ($15 \times 10^6$ per mouse) were injected (i.v.) into 6 week NOD.Scid females (Jackson Labs) together with $3 \times 10^6$ CD4+ T-cells from mice either treated with the EGAD-BPI or treated identically except with PBS in place of the EGAD-BPI. In vitro clonal expansion was with either recombinant IL-2 (R&D systems), or ConA, as described for the ELISPOT experiments. All manipulations of animals and cells were performed in laminar flow hoods, and animals were maintained continuously behind laminar flow barriers on autoclaved food and water in microisolator cages. Some experiments will deplete specific subsets of the CD4+ cells using mAb to CD154, CD25, CD62L, CD152, etc. and magnetic particles prior to adoptive transfer. CD4+ cells from mice treated with the individual moieties of the BPI can be used as negative controls along with CD4+ cells from mice treated with saline alone. Co-transfer of CD4+ T-cells enriched from matched NOD mice treated with a given BPI demonstrates that BPI treatment leads to regulatory T-cells capable of delaying the onset of diabetes. Moreover, other diseases listed in Table 1 can be tested in this same manner (i.e., by adoptive transfer of regulatory T-cells).

Figure 13:
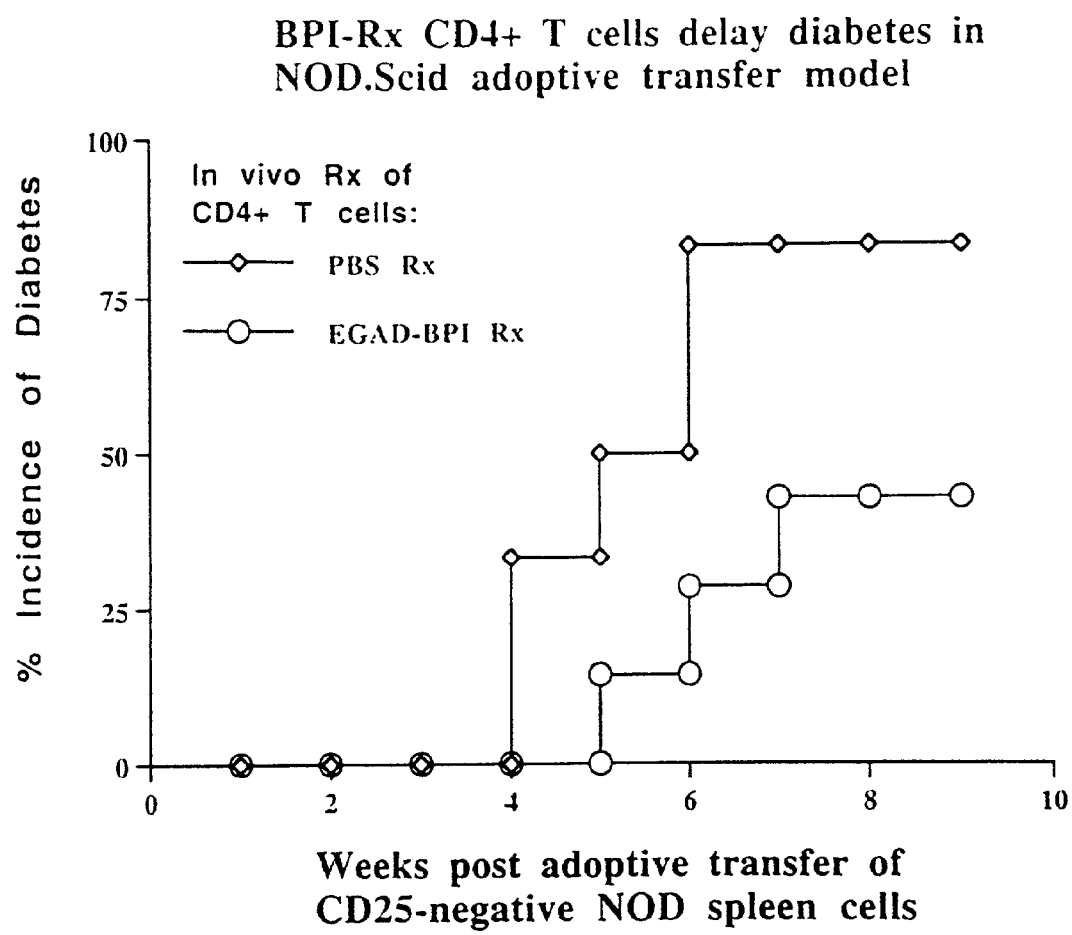
FIG. 13 is a graph illustrating the results of a 10 week monitoring of blood glucose levels in NOD.Scid mice which received CD25-negative diabetes-inducer cells together with T-cells from NOD mice injected with either the EGAD-BPI or saline.

Results:

Significantly, we have now seen a clear difference in the development of hyperglycemia and diabetes between the two experimental groups. As can be seen in FIG. 13, at 7 weeks post adoptive transfer, 80% of mice which received the vehicle, (PBS) developed hyperglycemia and diabetes. By contrast only 40% of mice treated with the EGAD-BPI showed hyperglycemia and progression to diabetes. Therefore, these data demonstrate the blocking of diabetes progression as mediated by the BPI treatment. Further modifications to the BPI structure may enhance their effectiveness in this model and in the treatment of type-1 diabetes. These data indicate that T-cells capable of suppressing diabetes development were generated in the presence of the BPI and operated in vivo to inhibit diabetes progression within the intact system of the NOD.Scid mouse. Thus we would anticipate similar regulatory T-cells to become activated by BPI containing TCR epitopes of other disease associated antigens. For example, collagen-II peptide epitopes may initiate suppressor T-cells involved in rheumatoid arthritis. Moreover, regulatory T-cells that would expand $T_H1$ populations may be generated by BPI containing CTLA4 second signal moieties and these could be used in diseases such as HIV1 infection or other chronic viral diseases. Extrapolation of this example to clinical trial should be straightforward, as the NOD model is recognized as a significant representation of the human disease. (See e.g., Atkinson and Leiter, The NOD Mouse Model of Type-1 Diabetes: As Good as it Gets?, 5 *Nature Medicine*, 601-604 (1999).

EXAMPLE 7

Here, the predicted examples of BPI for other autoimmune diseases are briefly detailed. Specifically, BPI containing immunodominant TCR epitopes for collagen-induced arthritis (CIA) and myelin basic protein-induced experimental allergic encephalomyelitis (EAE) will be discussed. Also, the CD40L peptide mimic is predicted to favor $T_H2$ immunity, as blocking the CD40 signal would be expected to decrease IL12 production (Ruedl, et al., *The Antigen Dose Determines T Helper Subset Development by Regulation of CD40 Ligand*, 30 Eur. J. Inmunol. 2056-2064 (2000)). Therefore, in these autoimmune models and in the NOD model, we will attempt to favor $T_H2$ immunity by linking the appropriate TCR epitopes to the CD40L peptide mimic as well as the CD11 mimic used in diabetes inhibition. Mutations in this loop peptide have been shown to affect binding and function of CD40L.

Materials and Methods:

There are several autoimmune models which employ different cross-reactive immunodominant epitopes, different mouse strains, and tissues of analysis. These types of models are highly similar to our short-term model of diabetes development that we designed to test the EGAD-BPI. For CIA: We will induce the disease by a single peptide in CFA injection protocol as described by Murray et al., 24 *Eur. J. Immunol.* 2337-2344 (1994). As in the NOD system, these mice will receive either the BPI, PBS, or the single peptide moieties. The minimal immunodominant collagen-II epitope is listed above, and modifications to the BPI will be based upon the x-ray structure of this complex (Dessen et al., 7 Immunity 473-481 (1997). For EAE, the disease is induced by the method of Murray et al., 24 *Eur. J. Immunol.* 2337-2344 (1994). This method also uses a single peptide (the myelin basic protein (MBP) peptide, 85-101) injection in CFA, by methods analogous to those described in our NOD system.

Results:

We would anticipate that the BPI constructed with collagen and MBP would be effective in modulating immunity to these antigens to a $T_H2$-dominated pattern. Since these diseases are thought to involve predominant $T_H1$ immunopathology (see above references), such a switch would ostensibly delay or cure the disease in these mice (Murray et al., 24 *Eur. J. Immunol.* 2337-2344 (1994); Murray; 19 *Immunology Today* 157-163; and Schountz et al., 157 *The Journal of Immunology* 3893-3901 (1996). As in the NOD model, such results would target the development of analogous compounds for use in the human diseases of rheumatoid arthritis and multiple sclerosis, where these types of immune responses are clinically observed. Most importantly, BPI offer the capability of blocking autoimmune T-cell responses while maintaining host immunity to infectious agents and developing cancers.

EXAMPLE 8

This example describes predicted BPI for infectious diseases and certain cancers. Specifically, a general protocol for the testing of a given BPI containing immunodominant TCR epitopes of a specific human pathogen will be described using the example of HIV-1 p24 epitope (Harcourt, et. al., *HIV-1 Variation Diminishes CD4 T Lymphocyte Recognition*, 188 J. Exp. Med., 1785-1793 (1998)) (SEQ ID No. 8).

Materials and Methods:

By contrast to the previous experimental examples, these BPI will be primarily tested by their effects on long-term T-cell clones derived from human patients. Briefly, peripheral blood mononuclear cells (PBMCs) are prepared from patient and control whole blood, and CD8+ cells removed by the negative selection protocol with magnetic particles. These cells are grown in tissue culture medium at $4 \times 10^6$ cells in 1 ml for 6 days in the presence of 20 µM of the p24 peptide, and blast cells isolated by density gradient centrifugation. Secondary cultures of these cells contained recombinant human IL-2 (20 U/ml) and are continued for a maximum of 10-14 days. Lines were expanded by repeating the process of re-culturing with irradiated APC from histocompatible donors together with the p24 peptide and expansion of the T-cell blasts in IL-2. Clones were prepared by limiting dilution cloning in fresh plates containing irradiated APC, peptide and IL-2 (50 U/ml) (Murray et al., 24 *Eur. J. Immunol.* 2337-2344 (1994); Murray; 19 *Immunology Today* 157-163; and Schountz et al., 157 *The Journal of Immunology* 3893-3901 (1996)). BPI will be tested for their ability to inhibit the proliferation and cytokine release of these established lines of human T-cells by our detailed methods described in Schountz et al., *Unique T Cell Antagonist Properties of the Exact Self-Correlate of a Peptide Antigen Revealed by Self-Substitution of Non-Self-Positions in the Peptide Sequence,* 168 Cellular Immunology 193-200 (1996). Here, we show that pe -continued <213> ORGANISM: Homo sapiens

<400> SEQUENCE: 1

Glu Ile Ala Pro Val Phe Val Leu Leu Glu
1               5                   10

<210> SEQ ID NO 2
<211> LENGTH: 10
<212> TYPE: PRT
<213> ORGANISM: Mus musculus

<400> SEQUENCE: 2

Glu Ile Ala Pro Val Phe Val Leu Leu Glu
1               5                   10

<210> SEQ ID NO 3
<211> LENGTH: 13
<212> TYPE: PRT
<213> ORGANISM: Homo sapiens

<400> SEQUENCE: 3

Gln Tyr Met Arg Ala Asp Gln Ala Ala Gly Gly Leu Arg
1               5                   10

<210> SEQ ID NO 4
<211> LENGTH: 12
<212> TYPE: PRT
<213> ORGANISM: Yersinia enterocolitica

<400> SEQUENCE: 4

Arg Val Val Ile Asn Lys Asp Thr Thr Ile Ile Ile
1               5                   10

<210> SEQ ID NO 5
<211> LENGTH: 15
<212> TYPE: PRT
<213> ORGANISM: Homo sapiens

<400> SEQUENCE: 5

Glu Asn Pro Val Val His Phe Phe Lys Asn Ile Val Thr Pro Arg
1               5                   10                  15

<210> SEQ ID NO 6
<211> LENGTH: 14
<212> TYPE: PRT
<213> ORGANISM: Hepatitis C virus

<400> SEQUENCE: 6

Gly Tyr Lys Val Leu Val Leu Asn Pro Ser Val Ala Ala Thr
1               5                   10

<210> SEQ ID NO 7
<211> LENGTH: 20
<212> TYPE: PRT
<213> ORGANISM: Human immunodeficiency virus type 1

<400> SEQUENCE: 7

Gly Ser Asp Thr Ile Thr Leu Pro Cys Arg Ile Lys Gln Phe Ile Asn
1               5                   10                  15

Met Trp Gln Glu
            20

<210> SEQ ID NO 8
<211> LENGTH: 20

<212> TYPE: PRT
<213> ORGANISM: Human immunodeficiency virus type 1

<400> SEQUENCE: 8

```
Pro Ile Val Gln Asn Leu Gln Gly Gln Met Val His Gln Ala Ile Ser
 1               5                  10                  15

Pro Arg Thr Leu
            20
```

<210> SEQ ID NO 9
<211> LENGTH: 8
<212> TYPE: PRT
<213> ORGANISM: Simian immunodeficiency virus

<400> SEQUENCE: 9

```
Ser Thr Pro Glu Ser Ala Asn Leu
 1               5
```

<210> SEQ ID NO 10
<211> LENGTH: 15
<212> TYPE: PRT
<213> ORGANISM: respiratory syncytial virus

<400> SEQUENCE: 10

```
Ala Ile Cys Lys Arg Ile Pro Asn Lys Lys Pro Gly Lys Lys Thr
 1               5                  10                  15
```

<210> SEQ ID NO 11
<211> LENGTH: 9
<212> TYPE: PRT
<213> ORGANISM: Human papillomavirus

<400> SEQUENCE: 11

```
Val Tyr Arg Asp Gly Asn Pro Tyr Ala
 1               5
```

<210> SEQ ID NO 12
<211> LENGTH: 7
<212> TYPE: PRT
<213> ORGANISM: Human papillomavirus

<400> SEQUENCE: 12

```
Asp Arg Ala His Tyr Asn Ile
 1               5
```

<210> SEQ ID NO 13
<211> LENGTH: 10
<212> TYPE: PRT
<213> ORGANISM: Human papillomavirus

<400> SEQUENCE: 13

```
Tyr Met Leu Asp Leu Gln Pro Glu Thr Thr
 1               5                  10
```

<210> SEQ ID NO 14
<211> LENGTH: 15
<212> TYPE: PRT
<213> ORGANISM: Human papillomavirus

<400> SEQUENCE: 14

```
Ala Ser Asp Leu Arg Thr Ile Gln Gln Leu Leu Met Gly Thr Val
 1               5                  10                  15
```

<210> SEQ ID NO 15

```
<211> LENGTH: 13
<212> TYPE: PRT
<213> ORGANISM: Homo sapiens

<400> SEQUENCE: 15

Ala Glu Leu Tyr His Phe Leu Leu Lys Tyr Arg Ala Arg
 1               5                  10

<210> SEQ ID NO 16
<211> LENGTH: 14
<212> TYPE: PRT
<213> ORGANISM: Homo sapiens

<400> SEQUENCE: 16

Leu Leu Lys Tyr Arg Ala Arg Glu Pro Val Thr Lys Ala Glu
 1               5                  10

<210> SEQ ID NO 17
<211> LENGTH: 16
<212> TYPE: PRT
<213> ORGANISM: Felis sp.

<400> SEQUENCE: 17

Glu Gln Val Ala Gln Tyr Lys Ala Leu Pro Val Val Leu Glu Asn Ala
 1               5                  10                  15

<210> SEQ ID NO 18
<211> LENGTH: 17
<212> TYPE: PRT
<213> ORGANISM: Felis sp.

<400> SEQUENCE: 18

Lys Ala Leu Pro Val Val Leu Glu Asn Ala Arg Ile Leu Lys Asn Cys
 1               5                  10                  15

Val

<210> SEQ ID NO 19
<211> LENGTH: 20
<212> TYPE: PRT
<213> ORGANISM: Ambrosia artemisiifolia

<400> SEQUENCE: 19

Leu Val Pro Cys Ala Trp Ala Gly Asn Val Cys Gly Glu Lys Arg Ala
 1               5                  10                  15

Tyr Cys Cys Ser
            20

<210> SEQ ID NO 20
<211> LENGTH: 20
<212> TYPE: PRT
<213> ORGANISM: Ambrosia trifida

<400> SEQUENCE: 20

Pro Ile Gly Lys Tyr Cys Val Cys Tyr Asp Ser Lys Ala Ile Cys Asn
 1               5                  10                  15

Lys Asn Cys Thr
            20

<210> SEQ ID NO 21
<211> LENGTH: 15
<212> TYPE: PRT
<213> ORGANISM: Cryptomeria japonica

<400> SEQUENCE: 21
```

```
Lys Ser Met Lys Val Thr Val Ala Phe Asn Gln Phe Gly Pro Asn
  1               5                  10                 15
```

<210> SEQ ID NO 22
<211> LENGTH: 19
<212> TYPE: PRT
<213> ORGANISM: Cryptomeria japonica

<400> SEQUENCE: 22

```
Ile Asp Ile Phe Ala Ser Lys Asn Phe His Leu Gln Lys Asn Thr Ile
  1               5                  10                  15

Gly Thr Gly
```

<210> SEQ ID NO 23
<211> LENGTH: 17
<212> TYPE: PRT
<213> ORGANISM: Apis mellifera

<400> SEQUENCE: 23

```
Tyr Phe Val Gly Lys Met Tyr Phe Asn Leu Ile Asp Thr Lys Cys Tyr
  1               5                  10                  15

Lys
```

<210> SEQ ID NO 24
<211> LENGTH: 20
<212> TYPE: PRT
<213> ORGANISM: Hevia brasiliensis

<400> SEQUENCE: 24

```
Ala Ser Glu Gln Glu Thr Ala Asp Ala Thr Pro Glu Lys Glu Glu Pro
  1               5                  10                  15

Thr Ala Ala Pro
             20
```

<210> SEQ ID NO 25
<211> LENGTH: 17
<212> TYPE: PRT
<213> ORGANISM: Dermatophagoides pteronyssinus

<400> SEQUENCE: 25

```
Phe Gly Ile Ser Asn Tyr Cys Gln Ile Tyr Pro Pro Asn Ala Asn Lys
  1               5                  10                  15

Ile
```

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      Linker
<220> FEATURE:
<221> NAME/KEY: MOD_RES
<222> LOCATION: (1)
<223> OTHER INFORMATION: aminocaproic acid
<220> FEATURE:
<221> NAME/KEY: MOD_RES
<222> LOCATION: (3)
<223> OTHER INFORMATION: aminocaproic acid
<220> FEATURE:
<221> NAME/KEY: MOD_RES
<222> LOCATION: (5)
<223> OTHER INFORMATION: aminocaproic acid

<400> SEQUENCE: 26

Xaa Gly Xaa Gly Xaa
 1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      Linker
<220> FEATURE:
<221> NAME/KEY: MOD_RES
<222> LOCATION: (1)
<223> OTHER INFORMATION: aminocaproic acid
<220> FEATURE:
<221> NAME/KEY: MOD_RES
<222> LOCATION: (3)
<223> OTHER INFORMATION: beta-alanine
<220> FEATURE:
<221> NAME/KEY: MOD_RES
<222> LOCATION: (5)
<223> OTHER INFORMATION: aminocaproic acid

<400> SEQUENCE: 27

Xaa Gly Xaa Gly Xaa
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      Linker
<220> FEATURE:
<221> NAME/KEY: MOD_RES
<222> LOCATION: (1)
<223> OTHER INFORMATION: aminocaproic acid
<220> FEATURE:
<221> NAME/KEY: MOD_RES
<222> LOCATION: (3)
<223> OTHER INFORMATION: aminododecanoic acid
<220> FEATURE:
<221> NAME/KEY: MOD_RES
<222> LOCATION: (5)
<223> OTHER INFORMATION: aminocaproic acid

<400> SEQUENCE: 28

Xaa Gly Xaa Gly Xaa
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      Linker
<220> FEATURE:
<221> NAME/KEY: MOD_RES
<222> LOCATION: (1)
<223> OTHER INFORMATION: aminohexanoic acid
<220> FEATURE:
<221> NAME/KEY: MOD_RES
<222> LOCATION: (3)
<223> OTHER INFORMATION: aminohexanoic acid
<220> FEATURE:
<221> NAME/KEY: MOD_RES
<222> LOCATION: (5)
<223> OTHER INFORMATION: aminohexanoic acid

<400> SEQUENCE: 29

```
Xaa Gly Xaa Gly Xaa
1               5

<210> SEQ ID NO 30
<211> LENGTH: 10
<212> TYPE: PRT
<213> ORGANISM: Homo sapiens

<400> SEQUENCE: 30

Ile Thr Asp Gly Glu Ala Thr Asp Ser Gly
1               5                   10

<210> SEQ ID NO 31
<211> LENGTH: 10
<212> TYPE: PRT
<213> ORGANISM: Homo sapiens

<400> SEQUENCE: 31

Thr Asp Gly Glu Ala Thr Asp Ser Gly Asn
1               5                   10

<210> SEQ ID NO 32
<211> LENGTH: 10
<212> TYPE: PRT
<213> ORGANISM: Homo sapiens

<400> SEQUENCE: 32

Ala Ser Pro Gly Lys Ala Thr Glu Val Arg
1               5                   10

<210> SEQ ID NO 33
<211> LENGTH: 10
<212> TYPE: PRT
<213> ORGANISM: Mus musculus

<400> SEQUENCE: 33

Ser Pro Ser His Asn Thr Asp Glu Val Arg
1               5                   10

<210> SEQ ID NO 34
<211> LENGTH: 12
<212> TYPE: PRT
<213> ORGANISM: Homo sapiens

<400> SEQUENCE: 34

Lys Val Glu Leu Met Tyr Pro Pro Tyr Tyr Leu
1               5                   10

<210> SEQ ID NO 35
<211> LENGTH: 12
<212> TYPE: PRT
<213> ORGANISM: Mus musculus

<400> SEQUENCE: 35

Lys Val Glu Leu Met Tyr Pro Pro Tyr Phe Val
1               5                   10

<210> SEQ ID NO 36
<211> LENGTH: 10
<212> TYPE: PRT
<213> ORGANISM: Mus musculus

<400> SEQUENCE: 36

Ile Thr Asp Gly Glu Ala Thr Asp Ser Gly
1               5                   10
```

<210> SEQ ID NO 37
<211> LENGTH: 13
<212> TYPE: PRT
<213> ORGANISM: Homo sapiens

<400> SEQUENCE: 37

Lys Gly Tyr Tyr Thr Met Ser Asn Asn Leu Val Thr Leu
1               5                   10

<210> SEQ ID NO 38
<211> LENGTH: 13
<212> TYPE: PRT
<213> ORGANISM: Mus musculus

<400> SEQUENCE: 38

Lys Gly Tyr Tyr Thr Met Ser Asn Asn Leu Val Thr Leu
1               5                   10

<210> SEQ ID NO 39
<211> LENGTH: 16
<212> TYPE: PRT
<213> ORGANISM: Homo sapiens

<400> SEQUENCE: 39

Tyr Met Arg Asn Ser Lys Tyr Arg Ala Gly Gly Ala Tyr Gly Pro Gly
1               5                   10                  15

<210> SEQ ID NO 40
<211> LENGTH: 16
<212> TYPE: PRT
<213> ORGANISM: Mus musculus

<400> SEQUENCE: 40

Tyr Met Arg Asn Ser Lys Tyr Arg Ala Gly Gly Ala Tyr Gly Pro Gly
1               5                   10                  15

<210> SEQ ID NO 41
<211> LENGTH: 10
<212> TYPE: PRT
<213> ORGANISM: Mus musculus

<400> SEQUENCE: 41

Thr Asp Gly Glu Ala Thr Asp Ser Gly Asn
1               5                   10

<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (11)
<223> OTHER INFORMATION: aminocaproic acid
<220> FEATURE:
<221> NAME/KEY: MOD_RES
<222> LOCATION: (13)
<223> OTHER INFORMATION: aminocaproic acid
<220> FEATURE:
<221> NAME/KEY: MOD_RES
<222> LOCATION: (15)
<223> OTHER INFORMATION: aminocaproic acid

<400> SEQUENCE: 42

```
Glu Ile Ala Pro Val Phe Val Leu Leu Glu Xaa Gly Xaa Gly Xaa Ile
 1               5                  10                  15

Thr Asp Gly Glu Ala Thr Asp Ser Gly
                20                  25

<210> SEQ ID NO 43
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (9)
<223> OTHER INFORMATION: aminocaproic acid
<220> FEATURE:
<221> NAME/KEY: MOD_RES
<222> LOCATION: (11)
<223> OTHER INFORMATION: aminododecanoic acid
<220> FEATURE:
<221> NAME/KEY: MOD_RES
<222> LOCATION: (13)
<223> OTHER INFORMATION: aminocaproic acid

<400> SEQUENCE: 43

Ser Thr Pro Glu Ser Ala Asn Leu Xaa Gly Xaa Gly Xaa Tyr Met Arg
 1               5                  10                  15

Asn Ser Lys Tyr Arg Ala Gly Gly Ala Tyr Gly Pro Gly
                20                  25

<210> SEQ ID NO 44
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (21)
<223> OTHER INFORMATION: aminocaproic acid
<220> FEATURE:
<221> NAME/KEY: MOD_RES
<222> LOCATION: (23)
<223> OTHER INFORMATION: aminocaproic acid
<220> FEATURE:
<221> NAME/KEY: MOD_RES
<222> LOCATION: (25)
<223> OTHER INFORMATION: aminocaproic acid

<400> SEQUENCE: 44

Pro Ile Val Gln Asn Leu Gln Gly Gln Met Val His Gln Ala Ile Ser
 1               5                  10                  15

Pro Arg Thr Leu Xaa Gly Xaa Gly Xaa Lys Val Glu Leu Met Tyr Pro
                20                  25                  30

Pro Pro Tyr Phe Val
                35

<210> SEQ ID NO 45
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (14)
<223> OTHER INFORMATION: aminocaproic acid
```

```
-continued

<220> FEATURE:
<221> NAME/KEY: MOD_RES
<222> LOCATION: (16)
<223> OTHER INFORMATION: aminohexanoic acid
<220> FEATURE:
<221> NAME/KEY: MOD_RES
<222> LOCATION: (18)
<223> OTHER INFORMATION: aminocaproic acid

<400> SEQUENCE: 45

Gln Tyr Met Arg Ala Asp Gln Ala Ala Gly Gly Leu Arg Xaa Gly Xaa
 1               5                  10                  15

Gly Xaa Lys Gly Tyr Tyr Thr Met Ser Asn Asn Leu Val Thr Leu
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (11)
<223> OTHER INFORMATION: aminocaproic acid
<220> FEATURE:
<221> NAME/KEY: MOD_RES
<222> LOCATION: (13)
<223> OTHER INFORMATION: aminocaproic acid
<220> FEATURE:
<221> NAME/KEY: MOD_RES
<222> LOCATION: (15)
<223> OTHER INFORMATION: aminocaproic acid

<400> SEQUENCE: 46

Tyr Met Leu Asp Leu Gln Pro Glu Thr Thr Xaa Gly Xaa Gly Xaa Tyr
 1               5                  10                  15

Met Arg Asn Ser Lys Tyr Arg Ala Gly Gly Ala Tyr Gly Pro Gly
            20                  25                  30
```

We claim:

1. A peptide comprising a first portion and a second portion, said first portion including a sequence having a peptide derived from a TCR epitope, said sequence selected from the group consisting of SEQ ID Nos. 1-25, said second portion including a sequence derived from a Signal-2 moiety, said sequence selected from a group consisting of SEQ ID Nos. 30-41.

2. The peptide of claim 1, further comprising a linking portion.

3. The peptide of claim 2, said linking portion comprising at least one amino acid residue.

4. The peptide of claim 3, said amino acid being a flexible, nonsubstrate amino acid.

5. The peptide of claim 2, said linking portion comprising a sequence of amino acid residues, said sequence comprising a non-substrate amino acid alternating with a hydrophilic amino acid.

6. The peptide of claim 2, said linking portion having the general formula $(A,B)_x$, wherein A and B are amino acid residues, and said A amino acid residue is individually and respectively selected from the group consisting of aminocaproic acid, aminohexanoic acid, aminododecanoic acid, and β-alanine, and said B amino acid residue is glycine, and wherein x ranges from 1 to 100.

7. The peptide of claim 6, said A amino acid residue being aminocaproic acid.

8. The peptide of claim 1, said TCR epitope being correlated with a known disease state.

9. The peptide of claim 1, said first portion capable of binding with a major histocompatability complex on an antigen presenting cell.

10. The peptide of claim 9, said peptide:MHC complex capable of engaging a T-cell receptor on a T-cell.

11. The peptide of claim 1, said second portion capable of binding with a Signal-2 ligand on an antigen presenting cell.

12. The peptide of claim 1, said peptide capable of modifying an immune response from a type-1 dominated response to a type-2 dominated response.

13. The peptide of claim 1, said peptide capable of modifying an immune response from a type-2 dominated response to a type-1 dominated response.

14. The peptide of claim 1, said second portion being associated with a particular type of immune response.

15. The peptide of claim 2, said linking portion being positioned intermediate said first portion and said second portion.

16. The peptide of claim 1, said peptide being synthesizable as one continuous sequence.

17. A peptide having the general formula AB wherein each of said A and B represent a chain of amino acid residues, and wherein said A chain comprises a sequence selected from the group consisting of SEQ ID Nos. 1-25 as a Signal-1 moiety, and said B chain comprises a sequence selected from the group consisting of SEQ ID Nos. 30-41 as a Signal-2 receptor moiety.

18. The peptide of claim 17, further comprising a linker of amino acid residues, said linker comprising at least 1 amino acid residue, said linker being positioned intermediate said A chain and said B chain.

19. The peptide of claim 17, said peptide being synthesizable as one continuous sequence.

20. The peptide of claim 18, said linker comprising a flexible, nonsubstrate linker having the general formula $(Y,Z)_t$, wherein Y and Z are amino acid residues, and said Y amino acid residue is individually and respectively selected from the group consisting of non-substrate amino acids, and said Z amino acid residue is individually and respectively selected from the group consisting of hydrophilic amino acids, and wherein t ranges from 1 to 100.

21. The peptide of claim 20, said non-substrate amino acids being selected from the group consisting of aminocaproic acid, aminohexanoic acid, aminododecanoic acid, and β-alanine.

22. The peptide of claim 21, said non-substrate amino acid residue being aminocaproic acid.

23. The peptide of claim 20, said hydrophilic amino acid being glycine.

24. The peptide of claim 17, said Signal-1 moiety being associated with a known health condition.

25. The peptide of claim 17, said peptide capable of binding with a major histocompatability complex on an antigen presenting cell to form a peptide:MHC complex.

26. The peptide of claim 25, said peptide:MHC complex capable of engaging a T-cell.

27. The peptide of claim 17, said peptide capable of binding with a Signal-2 ligand on an antigen presenting cell.

28. The peptide of claim 27, said peptide capable of blocking or altering a second signal to a T-cell upon binding with said Signal-2 moiety.

29. The peptide of claim 17, said peptide capable of modifying an immune response from a type-1 dominated response to a type-2 dominated response.

30. The peptide of claim 17, said peptide capable of modifying an immune response from a type-2 dominated response to a type-1 dominated response.

31. The peptide of claim 17, said peptide capable of shifting a cell-mediated immune response to a humoral immune response.

32. The peptide of claim 17, said peptide capable of shifting a humoral immune response to a cell-mediated response.

33. A peptide comprising:
a first peptide sequence selected from the group consisting of SEQ ID Nos 1-25 capable of initiating a first signal in a T-cell; and
a second peptide sequence selected from the group consisting of SEQ ID Nos. 30-41 capable of initiating a second signal in a T-cell.

34. The peptide of claim 33, further comprising a linking peptide sequence, said linking peptide sequence comprising at least one amino acid residue.

35. The peptide of claim 33, said first peptide sequence being derived from a Signal-1 moiety.

36. The peptide of claim 33, said second peptide sequence being derived from a Signal-2 receptor moiety.

37. The peptide of claim 34, said linking peptide sequence having the general formula of $(Y,Z)_t$, wherein Y and Z are amino acid residues, and wherein t ranges from 1 to 100.

38. The peptide of claim 37, said Y amino acid residue is individually and respectively selected from the group consisting of aminocaproic acid, aminohexanoic acid, aminododecanoic acid, and β-alanine.

39. The peptide of claim 37, said Z amino acid residue being individually and respectively selected from the group consisting of hydrophilic amino acid residues.

40. The peptide of claim 39, wherein said hydrophilic amino acid residue is glycine.

41. The peptide of claim 37, said Y amino acid residue being aminocaproic acid.

42. In combination:
a first peptide sequence selected from the group consisting of SEQ ID Nos. 1-25 capable of binding with a major histocompatibility complex on an antigen presenting cell; and a linker to
a second peptide sequence selected from the group consisting of SEQ ID Nos. 30-41 capable of binding with a Signal-2 ligand on an antigen presenting cell.

43. The combination of claim 42, said first peptide sequence being derived from a Signal-1 moiety.

44. The combination of claim 42, said second peptide sequence being derived from a Signal-2 receptor moiety.

45. The combination of claim 42, said linker comprising at least one amino acid residue.

46. The combination of claim 42, said linker having the general formula of $(Y,Z)_t$, wherein Y and Z are amino acid residues, and wherein t ranges from 1 to 100.

47. The combination of claim 46, wherein said Y amino acid residue is individually and respectively selected from the group consisting of aminocaproic acid, aminohexanoic acid, aminododecanoic acid, and β-alanine.

48. The combination of claim 47, said Y amino acid residue being aminocaproic acid.

49. The combination of claim 46, said Z amino acid residue being individually and respectively selected from the group consisting of hydrophilic amino acid residues.

50. The combination of claim 49, wherein said hydrophilic amino acid residue is glycine.

51. A peptide selected from the group consisting of SEQ ID Nos. 42-46.

* * * * *

UNITED STATES PATENT AND TRADEMARK OFFICE
CERTIFICATE OF CORRECTION

PATENT NO. : 7,786,257 B2
APPLICATION NO. : 09/739466
DATED : August 31, 2010
INVENTOR(S) : Joseph S. Murray, Teruna J. Siahaan and Yongbo Hu It is certified that error appears in the above-identified patent and that said Letters Patent is hereby corrected as shown below:

Column 51
Line 44, delete "including" and insert -- consisting of -- therefor.

Column 51
Line 47, delete "including" and insert -- consisting of -- therefor.

Column 52
Line 49, insert -- to form a peptide:MHC complex. -- after "presenting cell".

Column 52
Line 54, insert -- having a second portion consisting of a sequence selected from the group consisting of SEQ ID NO: 30, 31, 36, 37, 38, and 41 wherein said peptide is -- between "said peptide" and "capable of".

Column 52
Line 57, insert -- having a second portion consisting of a sequence selected from the group consisting of SEQ ID NO: 32-35 and 39-40 wherein said peptide is -- between "said peptide" and "capable of".

Column 52
Lines 60 and 61 – delete entire rows (Claim 14).

Column 53
Line 3, delete "comprises" and insert -- consists of -- therefor.

Column 53
Line 5, delete "comprises" and insert -- consists of -- therefor.

Column 53
Line 9, insert -- about -- between "at least" and "1 amino acid residue.".

Signed and Sealed this
Twenty-third Day of August, 2011

David J. Kappos
*Director of the United States Patent and Trademark Office*

Column 53
Line 10, delete "said linker being positioned intermediate said A chain and said B chain" and insert new claim: -- 19. The peptide of claim 18, said linker being positioned intermediate said A chain and said B chain --.

Column 53
Lines 39, 40 and 41 – delete entire rows (Claim 28).

Column 53
Line 42, insert -- having a B chain selected from the group consisting of SEQ ID NO: 30, 31, 36, 37, 38, and 41 wherein said peptide is -- between "said peptide" and "capable of".

Column 53
Line 45, insert -- having a B chain selected from the group consisting of SEQ ID NO: 32-35 and 39-40 wherein said peptide is -- between "said peptide" and "capable of".

Column 53
Lines 48 through 52 – delete entire rows (Claim 31 and Claim 32).

Column 54
Line 15, delete "individually and respectively" between "acid residue is" and "selected from".

Column 54
Line 26, insert -- linked to a second polypeptide sequence via a linker, said first polypeptide sequence consisting of a sequence -- between "peptide sequence" and "selected from".

Column 54
Line 30, delete "a" and insert -- said -- therefor.

Column 54
Line 30, insert -- consisting of a sequence -- between "peptide sequence" and "selected from".